(12) United States Patent
Han et al.

(10) Patent No.: US 12,633,403 B1
(45) Date of Patent: May 19, 2026

(54) SYSTEM AND METHOD FOR ARTIFICIAL-INTELLIGENCE-DRIVEN HEALTHCARE PRACTICE MANAGEMENT

(71) Applicant: HEALTH INTELLIGENCE LLC, Medina, WA (US)

(72) Inventors: Alison Han, Redmond, WA (US); Evgenii Viktorovich Bytsenko, Saint-Petersburg (RU)

(73) Assignee: HEALTH INTELLIGENCE LLC, Medina, WA (US)

( * ) Notice: Subject to any disclaimer, the term of this patent is extended or adjusted under 35 U.S.C. 154(b) by 0 days.

(21) Appl. No.: 18/629,272

(22) Filed: Apr. 8, 2024

Related U.S. Application Data

(60) Provisional application No. 63/457,724, filed on Apr. 6, 2023.

(51) Int. Cl.
G16H 40/20 (2018.01)
G06Q 10/0639 (2023.01)
(Continued)

(52) U.S. Cl.
CPC ....... G16H 40/20 (2018.01); G06Q 10/06393 (2013.01); G06Q 20/14 (2013.01); G10L 15/22 (2013.01); H04L 51/02 (2013.01)

(58) Field of Classification Search
CPC .. G16H 40/20; G06Q 10/06393; G06Q 20/14; G10L 15/22; H04L 51/02
See application file for complete search history.

(56) References Cited

U.S. PATENT DOCUMENTS

| | | | | |
|---|---|---|---|---|
| 11,323,196 B1 * | 5/2022 | Newton | ............... | H04B 7/0417 |
| 11,610,654 B1 * | 3/2023 | White | .................... | G16H 70/60 |

(Continued)

FOREIGN PATENT DOCUMENTS

| | | | | |
|---|---|---|---|---|
| WO | WO-2022198327 A1 * | 9/2022 | ............. | G16H 20/30 |

OTHER PUBLICATIONS https://web.archive.org/web/20230403122510/https://www.dentalintel. com/, cached on Apr. 3, 2023.

(Continued)

*Primary Examiner* — Shahid Merchant
*Assistant Examiner* — David Choi
(74) *Attorney, Agent, or Firm* — Leonid Kisselev

(57) ABSTRACT

Use of the cloud-based system and method described below that are driven by artificial intelligence empowers a healthcare practice by automating non-patient interfacing tasks and improving facility performance by analyzing staff performance against multiple metrics and providing individual recommendations to improve the performance, all while allowing the healthcare facilities to retain their existing practice management software. By increasing staff productivity and improving communication with the patient, the chance of the patient receiving required treatment increases, thus resulting in improved patient health outcomes. Further, by allowing healthcare facilities to retain their existing practice management software, the transition to use of the cloud-based system and method is simplified and impact of the learning curve on productivity is minimized. Thus, as a result of the use of the system and method, patient engagement is increased, while revenue cycle, care access, care delivery, and schedule of the healthcare facility are optimized.

19 Claims, 17 Drawing Sheets

(51) Int. Cl.
    *G06Q 20/14*          (2012.01)
    *G10L 15/22*          (2006.01)
    *H04L 51/02*          (2022.01)

(56)              References Cited

U.S. PATENT DOCUMENTS

| | | | |
|---|---|---|---|
| 2011/0301982 A1* | 12/2011 | Green, Jr. | G16H 40/67 |
| | | | 705/3 |
| 2017/0357759 A1* | 12/2017 | Stepaniuk | G06Q 50/18 |
| 2018/0324204 A1* | 11/2018 | McClory | G06F 9/5027 |
| 2019/0214134 A1* | 7/2019 | Bates | G06N 20/00 |
| 2020/0035335 A1* | 1/2020 | Kivatinos | G06F 17/16 |
| 2020/0160985 A1* | 5/2020 | Kusuma | G16H 30/40 |
| 2020/0211701 A1* | 7/2020 | Martindale | G16H 10/60 |
| 2021/0019834 A1* | 1/2021 | Sanjeevi | G06Q 40/08 |
| 2022/0116415 A1* | 4/2022 | Burgis | H04L 67/51 |
| 2022/0391270 A1* | 12/2022 | Gnanasambandam | |
| | | | G16H 20/70 |
| 2023/0140931 A1* | 5/2023 | Anderson | G06Q 40/08 |
| | | | 705/4 |
| 2023/0317260 A1* | 10/2023 | Zahora | G06Q 10/0639 |
| | | | 705/3 |

OTHER PUBLICATIONS https://web.archive.org/web/20230121181542/https://www.pattersondental.com/cp/software/dental-practice-management-software/eaglesoft#, cached on Jan. 21, 2023.

https://web.archive.org/web/20230313020227/https://www.opendental.com/site/version22_4.html, cached on Mar. 13, 2023.

https://web.archive.org/web/20230405174226/https://www.opendental.com/, cached on Apr. 5, 2023.

https://web.archive.org/web/20230316005329/https://www.henryscheinone.com/products/dentrix, cached on Mar. 16, 2023.

https://web.archive.org/web/20230323110300mp_/https://www.dentrix.com/products/dentrix, Mar. 23, 2023.

https://web.archive.org/web/20230323081409/https://www.dentrix.com/products/eservices, cached on Mar. 23, 2023.

https://web.archive.org/web/20221024182616/https://www.dentrix.com/products/dentrix-practice-advisor, cached on Oct. 24, 2022.

* cited by examiner

Figure 11:
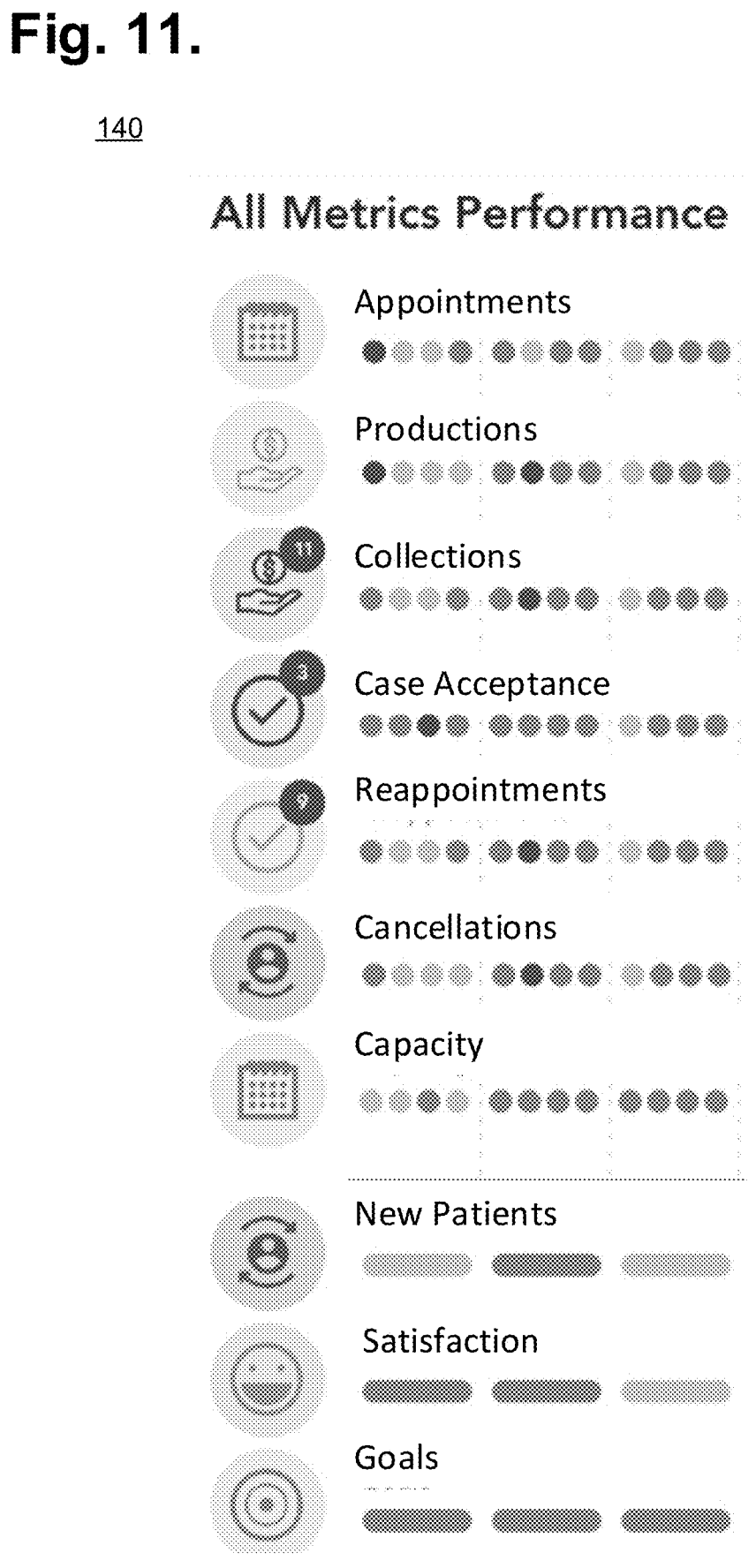

All Metrics Performance

Appointments

Productions

Collections

Case Acceptance

Reappointments

Cancellations

Capacity

New Patients

Satisfaction

Goals

150

160

170

180

190

200

SYSTEM AND METHOD FOR ARTIFICIAL-INTELLIGENCE-DRIVEN HEALTHCARE PRACTICE MANAGEMENT

FIELD

This application relates in general to healthcare technology, and in particular, to a system and method for artificial-intelligence-driven healthcare practice management.

BACKGROUND

Both healthcare facilities, such as dental and medical offices, and patients of those facilities face multiple challenges when receiving and administering healthcare services. On the provider side, such challenges relate to the amount of time necessary to comply with recording, billing, and administrative requirements that a healthcare provider needs to comply with when providing treatment to a patient. If performing a particular healthcare procedure takes an hour of the provider's time, checking the patient's insurance in relation to the procedure, writing a progress note for that procedure, identifying a correct billing code (or codes for the procedure) for the procedure, sending out bills and collection notices for the procedure, and other administrative tasks such as sending and receiving electronic mails and phone calls, explaining procedures, insurances and finances, updating in real-time registration, and obtaining consent forms, can consume multiple hours of time of the provider and other staff in the healthcare facility. Most of these tasks are manual have to be performed within a particular timeframe, adding further urgency to their completion. Patients seeking treatment face incomprehensible descriptions, restrictions, and maximums. Hence, on the patient side, this time burden results in a slowness with which the patient may receive information about both upcoming and past procedures, including the patient's responsibility for those procedures as staff members may not immediately have the requested information nor have the availability to provide the information even if the information is available. This slowness in turn results in a lack of transparency regarding the patient's healthcare process, and may lead to surprise elevated bills and result in the patient being inclined to delay or altogether forego a particular healthcare procedure, thus worsening the patient's health outcome.

The challenges described above, in addition to high staff shortage and turnover rate, are further exacerbated by the lack of systems, synchronization and data-literacy. Healthcare staff, such as doctors, dentists, nurses, assistants, and other personnel often lack objective data about their own performance, including how much time they spend on particular tasks, what are the draws on their productivity and efficiency. Most clinicians scheduled their appointment length based on habit, compliance and fears rather than based on knowledge and data. Without this knowledge and data, they lose the potential to improve their skills, to increase efficiency and effectiveness, thus, production and collection as they do not know what to improve, how to improve, and whether or not the improvements will negatively affect other sectors of the practice and to what the extent of the improvement needs to be implemented. For healthcare staff new to a particular clinic or the profession, these challenges are often even worse due to a lack of both knowledge of how a particular practice runs and lack of even a subjective knowledge of how efficiently they are spending their time. Also, in the case of dentistry, due to the arrival of dental service organizations (DSO), local dentists try to compete by opening multi-location clinics, further exacerbating the above-described challenges, multiplying these challenges into resounding impacts which can cause a company to undergo heavy financial stress and even bankruptcy.

While businesses have long tried to address of improving staff performance and increasing productivity, existing solutions have proven inadequate. For example, large companies establish systems that try to decrease the amount time needed to train their staff by tracking habits and performance. However, such an approach does not decrease the objective number of non-patient interfacing tasks that the healthcare personnel have to perform nor do they provide an objective way to improve the healthcare staff performance, thus being unable to substantially improve patient satisfaction. Similarly, some companies turn to coaching consultants, which are expensive and inefficient. In particular, coaching consultants generally cannot coach each staff member at an individual level not only due to the limitations of their own coaching enterprise (such as limited time, people, and staff attrition), but also because they lack sufficient knowledge of the healthcare practice in question, including data about patients, individual staff members, outcome correlations, and in case of dental practices, patient satisfaction knowledge. Likewise, the consultants are not able to reduce the number of non-patient-interfacing tasks that healthcare staff have to perform.

Others have turned to software to help address these challenges, but existing solutions are similarly lacking in many respects. For example, Dental Intelligence™ software distributed by Dental Intelligence, Inc. provided analyses a dental practice's performance and financial situation. The software also provides customer-managed relationship (CMR) capability and provides the dental practice information about the patients when they call. However, this software and other similar solutions provide intelligence regarding a dental practice as a whole, not individual staff members, and are thus inadequate in improving onboarding, coaching, and educating, as well as productivity and improving chances of retention of individual staff members. Further, while providing analysis, such solutions do not substantially reduce the non-patient interfacing tasks that the healthcare staff have to deal with.

Accordingly, there is a need for a real-time way to improve communication of procedure-related information to the patient, reduce the number of urgent non-patient interfacing tasks that healthcare staff have to perform, and improve productivity of individual staff members.

SUMMARY

Use of the cloud-based system and method described below that are driven by artificial intelligence empowers a healthcare practice by automating non-patient interfacing tasks and improving facility performance by analyzing staff performance against multiple metrics and providing individual institutional based actionable insights and education to improve the business performance, all while allowing the healthcare facilities to retain their existing practice management software. By increasing staff productivity and improving communication with the patient, the chance of the patient receiving required treatment increases, thus resulting in improved patient health outcomes and trust. Further, by allowing healthcare facilities to retain their existing practice management software, the transition to use of the cloud-based system and method is simplified and impact of the learning curve on productivity is minimized. Thus, as a result of the use of the system and method, patient engagement is increased, while revenue cycle, care access, care delivery, and schedule of the healthcare facility are optimized.

In one embodiment, a system for artificial-intelligence-driven healthcare practice management is provided. The system includes a cloud-computing environment that includes a plurality of servers, the servers including one or more frontend servers and one or more backend servers, each of the backend servers interfaced to at least one of the frontend servers, the cloud-computing environment further including: at least one of the frontend servers configured to receive data regarding an upcoming appointment for a healthcare procedure for a patient and information regarding insurance for the patient, the appointment data including a description of the procedure; one or more of the backend servers implementing a module utilizing artificial intelligence and configured to: use the artificial intelligence module to determine a billing code associated with the procedure using the description of the procedure; and determine a payment associated with the procedure that the patient is responsible for using the billing code and the insurance information; and send a message regarding the payment to a computing device associated with the patient via one of the frontend servers.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 7 is a diagram, showing by way of example, a user interface of the web portal 31 showing progress of the patient through a particular appointment.

FIG. 11 is a diagram showing, by way of example, a screenshot of a user interface of the web portal through which the KPIs are presented in graphical form.

DETAILED DESCRIPTION

Figure 1:
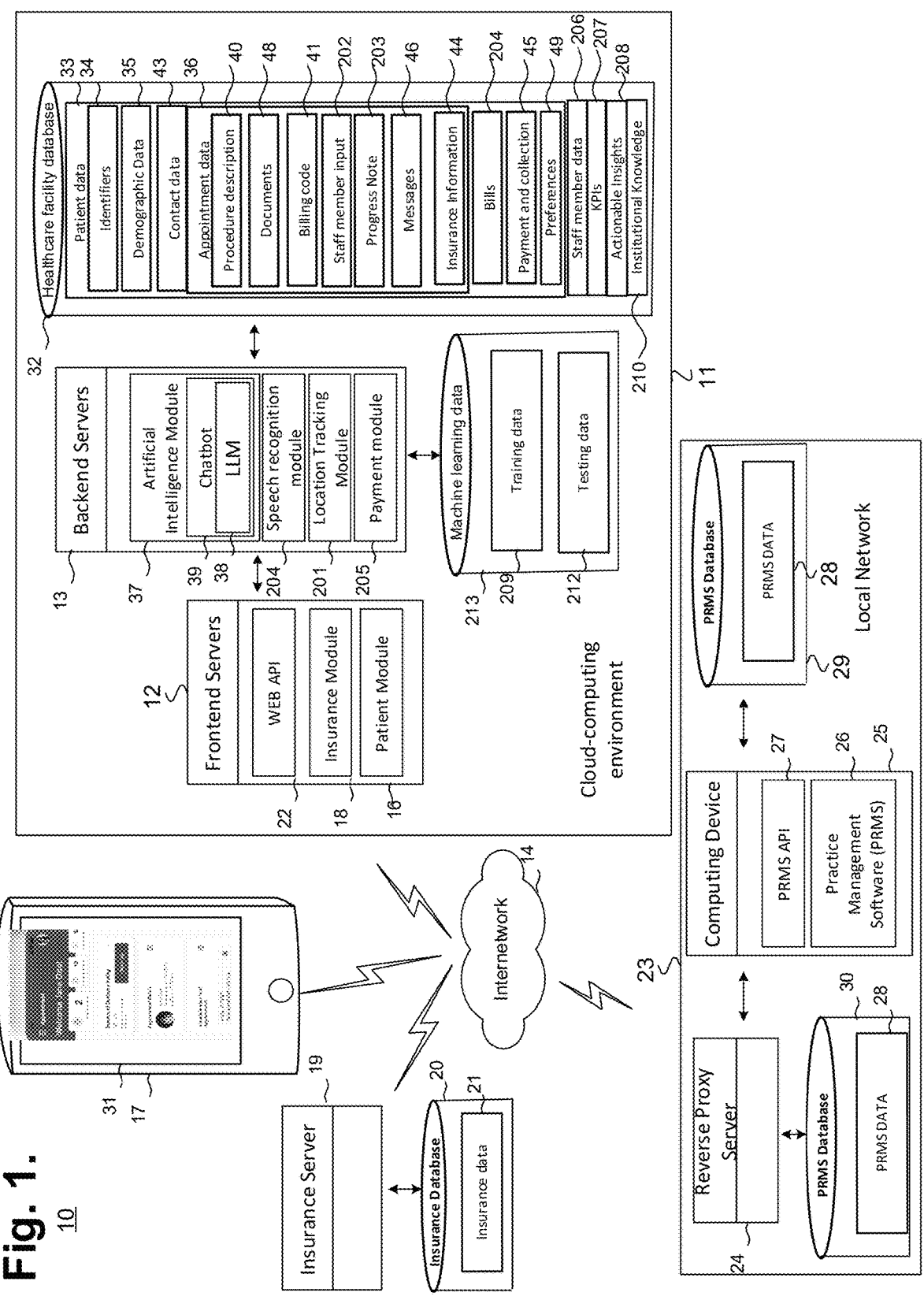
FIG. 1 is a block diagram showing a system for artificial-intelligence-driven healthcare practice management in accordance with one embodiment.

Patient satisfaction and outcomes and healthcare facility productivity can be increased through use of extensively-trained artificial intelligence utilizing resources of a cloud-environment and interacting with existing practice management software, insurance APIs, and private health information already used by the healthcare facility. While the description below focuses on dental and medical clinics (clinics ran by medical doctors, osteopathic doctors, or other providers having sufficient practice autonomy), the system and method described below can also be utilized for other healthcare providers. FIG. 1 is a block diagram showing a system 10 for artificial-intelligence-driven healthcare practice management in accordance with one embodiment. The system includes a cloud-computing environment 11, such as an environment that is implemented by Microsoft Azure®, provided by Microsoft Corporation of Redmond, Washington, though other cloud-computing environments 11 are possible. Inside the cloud-computing environment 11 are a plurality of servers 12, 13: frontend servers 12 and backend servers 13. In one embodiment, the frontend servers can utilize the Angular® (also known as Angular 2+) framework developed by Google LLC of Mountain View, California, though in a further embodiment, other frontend frameworks are also possible. In one embodiment, the backend servers 13 implement the .NET framework developed by Microsoft Corporation of Redmond, Washington, though in a further embodiment, other backend frameworks are possible. In one embodiment, the frontend 12 and backend servers 13 can be physical servers. In a further embodiment, at least a portion of the frontend 12 and backend servers can be virtual machines and can be implemented using docking containers and Kubernetes.

Figure 6:
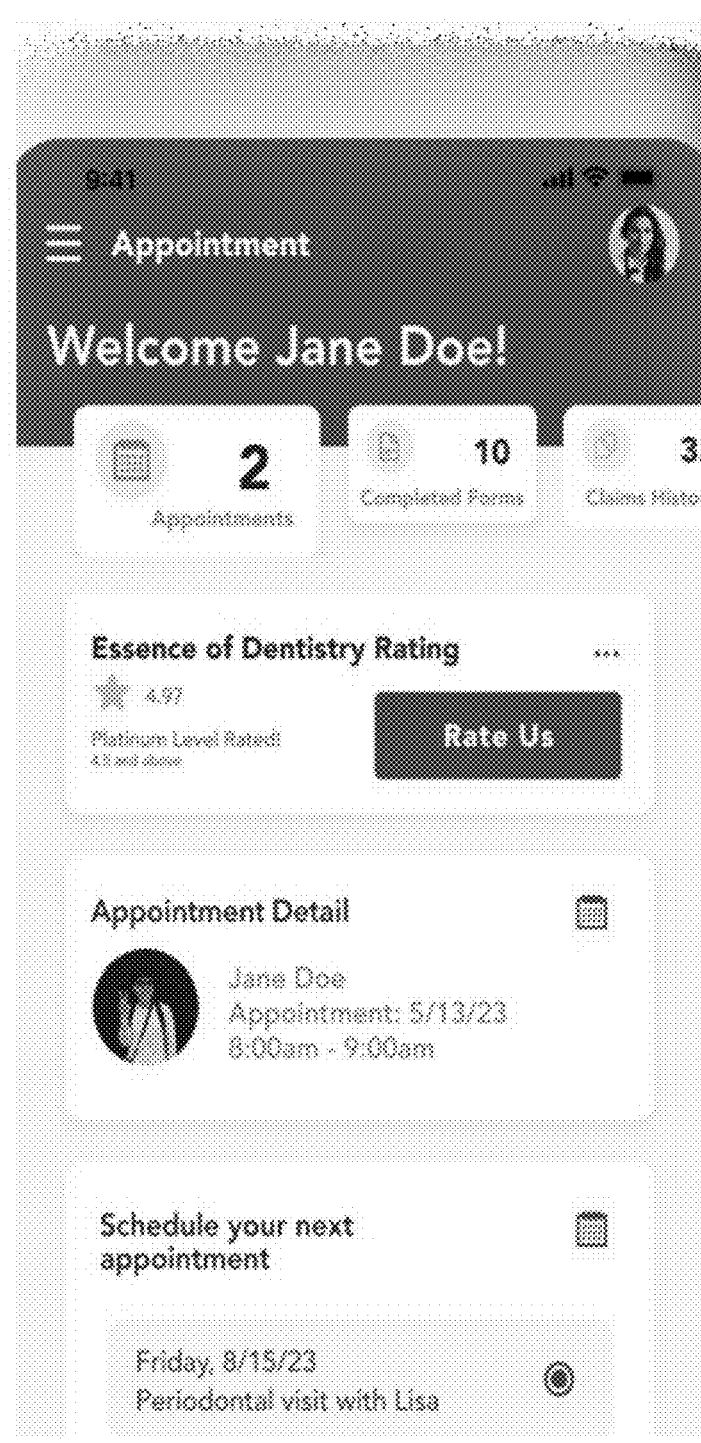
FIG. 6 is a diagram, showing by way of example, a user interface of a web portal presented through the computing device associate with the patient.

The frontend servers 12 communicate via one or more Internetwork 14 (such as the Internet or a cellular network) with computing devices outside of the cloud-computing environment 11. In particular, one or more of the frontend servers 12 execute a patient module 16 that can via one or more of the Internetworks communicate with a computing device 17 associated with a patient about an upcoming or past appointment for a healthcare procedure (such a dental or a medical procedure) for the patient. The computing device 17 can interface with the patient either through a web browser, or through a mobile application (though other ways for the interaction are also possible). Through interactions with the patient module 16, the computing device 17 can access a web portal 31 through which the patient, as further described below, can obtain permitted data that make the patient's healthcare process more transparent In a still further embodiment, the patient module 16 can interface with the computing device in other ways, such as e-mails, voice messages, video messages, and text messages. The data presented through the web portal 31 can include details regarding upcoming appointments for the patient's and the patient's previous history, as can be seen with reference to FIG. 6. FIG. 6 is a diagram, showing by way of example, a user interface 90 of a web portal 131 presented through the computing device associate with the patient.

One or more of the frontend servers 12 further executes an insurance module 18 that can interface via one or more of the Internetworks 14 to a server 19 connected to a database 20 of insurance data 21. The insurance data 21 includes details on which insurances a particular patient is associated with and the details of the patient's coverage, such as what percentage of a particular procedure is covered, and what is the patient's responsibility (including copay) for that procedure. In one embodiment, the insurance server 19 and the insurance database 20 can be associated with a clearing house that stores information of multiple insurance companies. In a further embodiment, the insurance server 19 and the insurance database 20 can be associated directly with an insurance company.

One or more of the frontend servers 12 further include execute a Web application programming interface (API) 22. The web API 22 communicates via an Internetwork with a local networks 23 of particular healthcare facilities. In particular, each of the local networks includes a reverse proxy server 24 (though in a further embodiment, the reverse proxy server dedicated to a particular local network can be located outside of that local network 23). The local networks 23 further include at least one computing device 25 (such as a server, though other kinds of computing devices are possible) that implements a practice management software (PRMS) 26 that is used by the healthcare staff in that facility. For example, a PRMS 26 can be Eaglesoft® software provided by Patterson Companies, Inc. of Saint Paul, MN; Open Dental® software owned by Open Dental Software, Inc. of Salem, Oregon; and Dentrix® Dental Systems software owned by Henry Schein, Inc. of American Fork, Utah, though other kinds of PRMS are also possible. The computing device 25 implementing the PRMS 26 further includes a PRMS API 27 that allows the reverse proxy server to request particular data 28 (such as data associated patients of that healthcare facility and data about performance of the healthcare facility) that is used by the PRMS 26 and that is stored in one or more separate databases 29. In one embodiment, the PRMS API can 27 can be a representational state transfer (REST) API, though in a further embodiment, other kinds of PRMS API are also possible. In a further embodiment, the computing device 25 can only include the PRMS 26 and not the PRMS API 27, and the reverse proxy server 24 directly requests the data from one or more of databases 30 storing the PRMS data 28. In communicating with the either the PRMS API or directly a PRMS database 30, the reverse proxy server 24 transforms requests received for PRMS data 28 received from the Web API 22 into a format usable by components of the local network 23. For example, the Web API 22 can receive request from another component of the system 10 for data associated with an appointment of a patient that is formatted with an external reference to a location within the local network: https://[server-name-do-main].com/eaglesoft/api/appointments/. The WEB API analyzes the request, determines the local network 23 of the healthcare facility the request is addressed to based on the analysis (such as based on the identifier of the healthcare facility included in the request to whose local network 23 the request is addressed, and provides the request to the reverse proxy server 24 that is assigned to interact with that local network. The reverse proxy server 24 reformats the request with a reference to the internal structure of the local network: https://localhost: 9888/api/appointments/ . . . . The reverse proxy server 24 retrieves the requested data 28 (either through the PRMS API 27 or directly from one of the PRMS databases 29) and provides the data 28 back to the Web API 28 along with the original request (https://[server-name-domain].com/eaglesoft/api/appointments/ . . . ), with the Web API 22 providing the received data 28 (with the original request) back to the requesting component. In addition to requesting PRMS data 28 based on requests from another components of the system 10, the WEB API 22 can periodically request certain highly-used data 28 from the local network 23. As components of the local network 23 can take a long time (such as 3-4 seconds) to provide the requested data 28, periodically requesting the data 28 in advance of when the data is needed allows to reduce the latency of the cloud-computing environment 11 when that data 28 is needed. The reverse proxy server 24 can similarly transform any reference accompanying PRSM data 28 that the PRSM 26 sends to the Web API without that data 28 being requested by the Web API 22. For example, if a user of the PRMS 26 from the healthcare facility initiates sending out data 28 to the cloud-computing environment 11 (such as to set up a new appointment or to update a status of an existing appointment), that data 28 is passed by the PRSM 26 to the PRSM API 27, which passes the data 28 to the reverse proxy server 24, which passes the data to the Web API 22, which in turn provides the data 28 to one or more of the backend servers 13. Further, the user of the PRMS 26 (either via the PRMS or through a separate computing device not executing the PRMS, such as the user's personal mobile phone) can request data stored in the cloud-computing environment 11 to be presented as a web portal 31 or through another kind of a user interface. In a further embodiment, the components that are described above and below as being part of the local network 23 could be implemented as part of another cloud-computing environment (not shown) associated with the healthcare facility. In this embodiment, the cloud-computing environment of which the servers 12, 13 and the databases 32, 213 are part of would be interacting with the cloud-computing environment implementing the PRMS 26, the reverse proxy server 24, the databases 29, 30, the PRMS API 27 and other components operated under the control of the healthcare facility.

In one embodiment, a single frontend server 12 can contribute to the execution of all of the Web API 22, the patient module 16, and the insurance module 18. The Alternatively, a single front end server contributes to execution of only one or two of the Web API 22, the patient module 16, and the insurance module 18.

The communication by the frontend servers is performed under a control of one or more of the backend servers 13 that perform processing of the received information, with the backend servers 13 receiving the data received by the frontend server 12 and providing at least a portion of the information to be sent by the frontend servers 12. The background servers are interfaced to a relational database 32 that stores data associated with only one of the healthcare facilities. The number of the relational databases corresponds to the number of healthcare facilities whose local networks 23 are registered with the cloud-computing environment 11 and the relational database 32 and the local network 23 that are associated with the same healthcare facility can be associated with the same healthcare facility identifier (not shown), with the background servers 13 using that healthcare facility identifier to direct data for one healthcare facility to the database 32 for that healthcare facility and request PRMS data 28 regarding that healthcare facility from the correct local network 23. In one embodiment, the relational database 32 can be executing a PostgreSQL relational database management system (RDBMS) developed by PostgreSQL Global Development Group, though in a further embodiment, other RDBMSes can also be executed by one or more of the relational databases 32.

The relational database 32 stores both information 33 that is associated with a patient and information regarding the healthcare facility associated with that database 32. The data 33 associated with the patient includes identifiers 34 associated with the patient. The patient identifiers 34 do not include the patient's last name to increase the patient's privacy protection. However, the identifiers 34 include an identifier used for the patient by the insurance server 18 (such as the patient's member ID and group number), an identifier used by the PRMS 26 (and with which the PRMS data 28 is associated), a first name of the patient, a birthdate of the patient. The identifiers 34 can further include a numeric or alphanumeric identifier that is unique to the cloud-computing environment 11. When interacting with the devices of the cloud-computing environment, the backend servers 13 (through the frontend servers 12) can provide the appropriate identifier 34 for all sent data to that device and receive the same identifier with from that device. For example, when interacting with the insurance server 19, the insurance module 18 provides to the insurance server 19 the patient's identifier 34 that is used by the patient's insurance (retrieved by one or more of the backend servers 13 from the relational database 34 and receives data regarding the patient's insurance with that same identifier 34. Likewise, when sending requests for PRMS data 28 to the local network 23, the frontend servers 12 include an identifier 34 that is used by the particular local network 23 for the patient in that request.

The data 33 can further include demographic information 35 for the patient, such as the patient's age and gender. Though other kinds of demographic data is also possible, such as whether the patient is employed, though still other kinds of demographic data is possible.

The data 33 further includes data 36 regarding appointments the patient has at the healthcare facility. Initially, a portion of the appointment data 36 is received from the local network 23 of the healthcare facility will happen, with the local network's PRMS 26 initiating the provision of some of the PRMS data 28 (at least some of which is set as the appointment data 36 in the relational database) to the cloud-computing environment 11 under a control of a user from that healthcare facility. The received PRSM data 28 can include a description 40 of the procedure to be performed, as further described below. The received PRMS data 28 can further include the scheduled time 42 (including time and date) for the for the appointment; alternatively, the scheduled time 42 can be determined by one or more of the background servers based on several options for openings provided as part of PRMS data 28, as further described below. The received PRSM data 28 can further include one or more identifiers of the patient, such as an identifier 34 of the patient within the local network 23 within which the PRSM data 28 originates; an identifier 34 of the patient with the patient's insurance company; the patient's first name. The PRSM data 28 can further include contact information 43 of the patient. The PRSM data 28 can further include the cost of the procedure to be performed during the appointment, which can be stored as part of payment and collection data 45 within the relational database 32 and used for calculating of patient and insurance responsibility. The received PRSM data 28 can further include patient preferences 49 (such as whether the patient prefers certain optional procedures to be done or whether the patient prefers a payment plan), which are stored in the relational database 32 (though the preferences can also be derived based on analysis of appointment data 36 for previous appointments of the patient). Other PRMS data 28 can also be received from the local network 23.

In addition to being received as part of PRMS data 28, the appointment data 36 can be received from the computing device 17 of the patient and generated by one or more of the backend servers 13. For example, one or more of the one or more of the backend servers implement an artificial intelligence module 37, which utilizes machine learning, including deep learning. One of the purposes of the artificial intelligence module 37 is utilizing a chatbot 39 that includes a large language model 38 (also referred to as "LLM") that can generate messages (such as text messages, though other formats are possible) and to convert textual descriptions into particular classifications. In one embodiment, the large language model 33 can be LLaMA-2 model released by META® AI (owned by Meta Platforms Inc. of New York City, New York), though in a further embodiment, other kinds of large language models 33 are also possible. The artificial intelligence module 37 receives from a local network 23 of one of the healthcare facilities (via the Web API 22) a description of the procedure 40 to be performed at an appointment for a patient. The artificial intelligence module 37 uses the large language model 38 to determine a billing code 41 (such as a CPT or CDT billing code) for the procedure based on the description of the procedure. For example, when the procedure is a dental procedure, the description includes a description of the tooth and the description of the surface of the tooth to which the procedure is done as well as the actions done to that surface. This description 40 can be abbreviated depending on industry practices. For example, the description of "posterior composite two surfaces" can be abbreviated as 4DO which the artificial intelligence module determines as corresponding to D2392 CDT billing code 41. While in the description below an appointment is referred to as being associated with a single procedure, multiple procedures (such as an exam, an X-ray, and a tooth treatment) can also be performed during a single appointment and thus a single appointment would be associated with multiple procedure descriptions 40 and multiple billing codes 41.

The large language model 38 and other classifying and predictive components of the components of the components are trained using training data 209. The training data 209 is heterogeneous due to the artificial intelligence module 37 using machine learning for different purposes and thus having to have been trained on different kinds of data. Thus, the training data 209 used to train the artificial intelligence module to convert the procedure description 40 into a billing code includes examples of procedure descriptions with associated billing code 41. Similarly, training data 209 used for other purposes includes examples of both input in association certain output data that are similar to the input data that the artificial intelligence module 37 will need to process. Prior to being used, the accuracy of the performance of the artificial intelligence module 37 is tested using testing data 212, which includes the same kind of data as the training data 209. For example, for performing conversions of the procedure descriptions 40 into billing codes, the testing data 212 provided to the artificial intelligence module 37 includes only procedure descriptions 40 and the artificial intelligence module converts the descriptions 40 into billing code 41. The accuracy of the converted billing codes 40 is compared to known billing codes 41 for the descriptions in the testing data 212 and if the accuracy falls below a threshold, additional training of the artificial intelligence module 37 is performed. The training data 209 and the testing data 212 are stored in a relational database 213 that is separate from relational databases 32 in which data associated with healthcare facilities is stored. In one embodiment, the database 213 can execute the PostgreSQL RDBSM, though other RDBMSes are also possible.

The artificial intelligence module 37 further sends (via the insurance module 18 and together with the patient's identifier 34 used by the insurance server 19) the identified billing code 41 to the insurance server 41 and retrieves the insurance data 21 that is related to the billing code 41. As insurance coverage can further depend on frequency of performance of a particular procedure and the last time the procedure was performed, the artificial intelligence module 37 further searches for appointment data 36 for previous appointments of the patient, and if any previous appointments with the same billing code are identified, provides this historical data regarding past appointments for which the same procedure was done to the insurance server 19 at the same time as the billing code 41. In response, the insurance server 19 provides to the artificial intelligence module 37 whether and how much the patient's insurance will pay for the procedure to be done at the appointment, which is stored as part of insurance information 44 for the appointment. Alternatively, the insurance server 19 can be provided the billing code 41 (along with the appropriate identifier 34 of the patient) and provides only the coverage details associated with that billing code 41 (which are also stored as part of the insurance information 44), with the artificial intelligence module 37 calculating how much the patient's insurance will pay for the procedure, the provided insurance details, and the historical data, with the calculated result being stored as part of the insurance information 44 in the relational database 32.

Based on the cost of the procedure and how much the insurance will pay for the appointment, the artificial intelligence module 37 calculates the patient financial responsibility for the appointment. For example, if the cost of the procedure is $500 and the patient's insurance will pay $350, the patient is responsible for the $150 of the cost. The patient's financial responsibility is stored as part of messages 46 that are sent by the chatbot to a computing device 17 of the patient. In particular, prior to confirming the time of the appointment with the patient, the chatbot 39 generates a layman description of the procedure using the description 40 provided by the PRSM 26 through the large language model 38 (which can be stored as part of the messages 46 in the relational database 32) and provides the patient with both the procedure description and the financial responsibility. If the patient is willing to schedule the appointment upon receipt of the laymen description and the financial responsibility, the chatbot 39 confirms the scheduled time 42 for the appointment. As further described below, if the healthcare facility performing the procedure has multiple available options for scheduling the appointment, the artificial intelligence module 39 confirms the scheduled time for the appointment based on (if available) the preferences of the provider performing the procedure, the patient's preferences communicated to the chatbot 37, and if flexibility exists, based on analysis of key performance indicators 47, as further described below. Acceptance of the scheduled time for the patient is also received through the chatbot 39.

Figure 8:
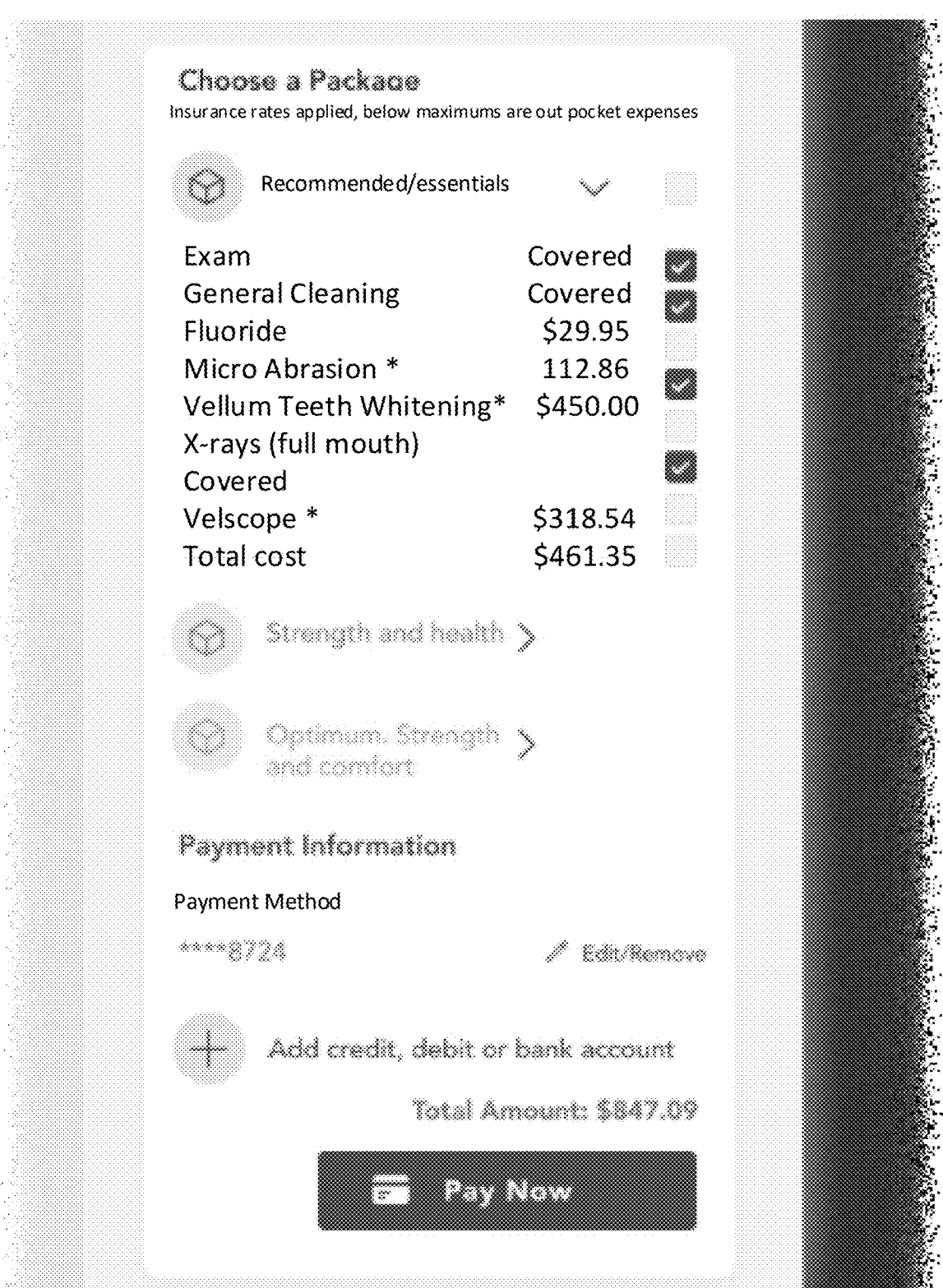
FIG. 8 is a diagram showing, by way of example, a user interface allowing the patient to choose particular procedures to be performed during an appointment.

In a further embodiment, if a particular procedure can have variations that have different costs or if multiple procedures can be performed within the same appointment, the patient can be offered a choice of what exactly is done via during the appointment and the associated costs. For example, if a yearly dental exam can include multiple procedures such as an X-ray, a teeth cleaning, a fluoride treatment, and micro-abrasion, the patient is presented with a choice of these procedures, as can be seen with reference to FIG. 8. FIG. 8 is a diagram showing, by way of example, a user interface 110 allowing the patient to choose particular procedures to be performed during an appointment.

In a further embodiment, in addition to determining the patient financial responsibility, the artificial intelligence module 37 can determine whether to offer the patient a payment plan, with such offer (stored as part of the messages 46) being provided prior to confirmation of the scheduled time for the appointment. Such determination can be made based upon the amount the patient has to pay (with the amount exceeding a threshold being a factor towards offering a payment plan), the patient's history of having payment plans for patient's other appointments, PRSM data 28 received and stored as part of the demographic data 35 that indicates the patient's income level Alternatively, the payment plan can be offered upon the chatbot 39 receiving such request from the computing device 17 associated with the patient. In one embodiment, the offering of a payment plan can require a confirmation from a user of the PRMS 26 of the healthcare facility to which payment is due. In a further embodiment, the payment plan can be offered by the artificial intelligence module 37 without requiring user confirmation.

The artificial intelligence module 37 module further identifies documents 48 (such as consent forms) that the patient needs to fill out prior to the procedure based on the description of the procedure 40 (or possibly the billing code). In one embodiment, the documents 48 are associated with a particular description of the procedure (or the billing code 41) as stored in the relational database. In a further embodiment, the artificial intelligence module 37 uses machine learning to classify certain documents 48 as being required for the procedure. The identified documents 48 are provided to the computing device 17 by the chatbot 39, with the patient being able to electronically fill out the documents on the computing device 17, with the computing device 17 providing the completed documents 48 to the chatbot 39 that stores the documents 48 within the database.

Further, if the patient has questions prior to or after the appointment regarding the appointment, the patient provides the questions to the chatbot 39 via the computing device 17. The chatbot 39 interprets the questions using natural language processing, and uses the large language model 38 to generate responses to the questions using data in the database 32, such as the patient's balance included as part of the payment and collections data 45, the patient's claim history with the healthcare facility (the appointment data 36 for previous appointments of the patient's, and the scheduled time 42 for the procedure. Other sources of information, such as sources outside of the cloud-computing environment 11 accessed via one or more of the Internetworks 14, can be accessed for answering the patient questions. The sources used for answering the questions depend on the questions—for example, if the question relates to the patient's balance with the healthcare facility, the chatbot 39 would use the payment and collection data 45 to answer the question. Likewise, if a question related to how far in advance the patient needs to leave the patient's house to arrive at the appointment in time, the chatbot 39 could use an Internet website outside of the cloud-computing environment 11 to determine the current traffic conditions.

Figure 7:
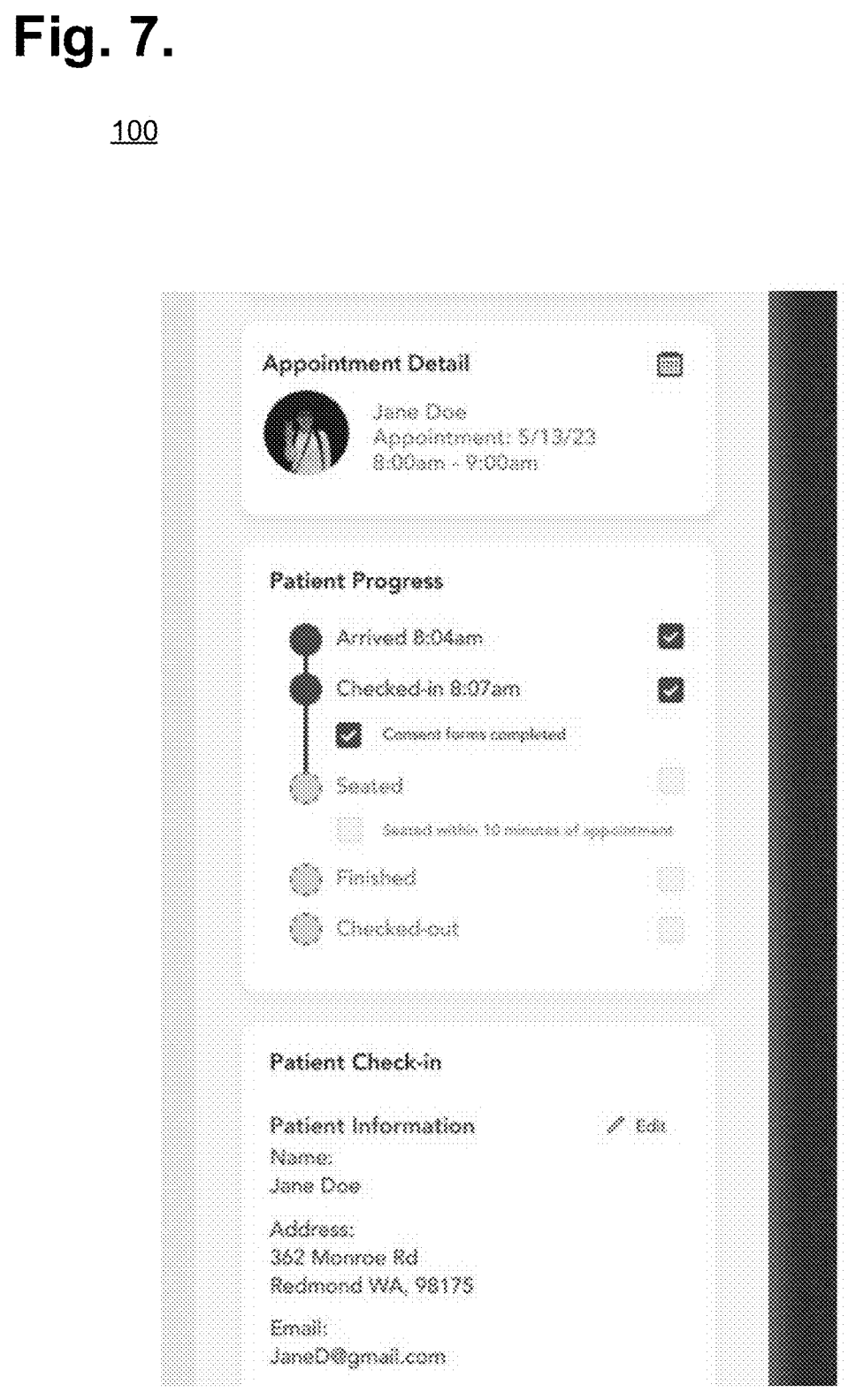

In addition, the chatbot 39 can generate messages 46 messages for the patient on real-time information related to the patient's appointment. For example, the backend servers 13 executes a location tracking module 201 that (with patient's explicit consent) tracks the patient's location to determine when the patient will arrive to the appointment through interactions with location tracking features of the patient's computing device 17 (such as a GPS receiver included in the computing device 17 if the device is a mobile phone). The determination of when the patient will arrive to the appointment can further utilize data from external sources, such as websites that provide traffic data. Depending on the patient's location, the chatbot 39 can generate one or more messages to the computing device 17 and the healthcare facility performing the appointment. For example, if the patient is running more than a predefined amount of time late to the appointment, the chatbot 39 can offer the patient to send a message 46 to the healthcare facility (either to a component of that healthcare facility's local network or to a further computing device (not shown) associated with one or more staff members at the healthcare facility) to notify the healthcare facility of the lateness. If the patient provides agreement through the computing device 17, the chatbot 39 sends the message 46 to the healthcare facility. In addition, the chatbot 39 can generate and provide one or more of the messages to the patient based on whether the healthcare facility will be late in seeing the patient. The determination can be made based on location tracking of one or more patient's whose appointment time preceded the appointment time of the patient in question; if the earlier patients have not left the healthcare facility when scheduled, then the next patient's appointment will be delayed and the chatbot 39 can provide a message 46 regarding the lateness to the patient. Alternatively, whether the patient's appointment will be late can be tracked based on user input 202 from the PRMS 26 of the healthcare facility. For example, the PRMS 26 (under control of a user from the healthcare facility) can provide PRMS data 28 to the chatbot 39 regarding whether the patient has arrived to the healthcare facility, whether the patient has been seated, and whether the patient's appointment has ended. The chatbot 39 can thus generate and send messages 46 based on progress of other patient's determined based on the received PRMS data 28. The progress of the patient through an appointment can be made available to both the patient and users associated with the healthcare facility through the web portal, as can be seen with reference to FIG. 7. FIG. 7 is a diagram, showing by way of example, a user interface 100 of the web portal 31 showing progress of the patient through a particular appointment.

The artificial intelligence module 39 further reduces the administrative burden related to the preparing progress notes 203 for the appointment. A progress note 203 is the provider's description of what occurred during an appointment and generally must follow particular formatting and guidelines. Writing out the full progress note 203 is time consuming for the provider. However, the provider can provide (as part of PRMS data 28 received from the PRMS 26 of the healthcare facility) user input 202 that includes the facts of what occurred during the appointment (such as what findings were discovered and what actions were performed to the patient) and the artificial intelligence module 37 can use the large language model 38 and natural language processing to prepare a full progress note 203 for the procedure that complies with the applicable formatting and stylistic requirements. The user input 202 with the facts can be provided as text. Alternatively, to further reduce the time commitment for the provider, the user input 202 as a voice recording from the provider, with at least one of the background servers 13 implementing a speech recognition module 204 that converts the voice recording into text usable by the artificial intelligence module 37.

Following the completion of the appointment, the artificial intelligence module 37 can further facilitate billing and collections for the appointment. In particular, depending on what occurred during a procedure, if the procedure is a medical procedure (a procedure performed by a physician such as a medical or osteopathic doctor), an enhancer code 41 of the original billing code 41 can be determined based on the progress note 203 using the large language model 38. The artificial intelligence module 39 can provide this enhancer code 41, along with the original billing code 41, as part of a recommendation for generating a bill 204 for the procedure that gets sent to the insurance company of the patient. In one embodiment, the recommendation for the bill 204 to be sent to the insurance company can include only the billing codes 41. In a further embodiment, the artificial intelligence module 37 can generate using the large language model the entire bill 204 to be sent and provide this bill 41 to the PRMS for confirmation by the appropriate staff member. In a still further embodiment, the PRMS 26 can provide a draft bill 41 to the artificial intelligence module 37, and the artificial intelligence module 37 can analyze the bill to detect (and notify the PRMS 26 of) any discrepancies between the billing codes 41 for the appointment and the bill 204. The artificial intelligence module 37 provides the bill 204 to the insurance company either through the insurance server 19 or through another medium. Likewise, based on the amount calculated for patient's financial responsibility, the artificial intelligence module 37 can provide a recommendation for a bill to be sent the patient (such as through creating a draft bill subject to the confirmation by a PRMS 26 user using the large language model 38, reviewing a bill 41 provided by the PRMS 26, or providing only the amount due from the patient based on which the PRMS 26 generates the bill 41) and provides the bill to the patient either through the computing device 17 or through another medium. Similarly to the bills 41 being subject to approval by a user associated with the local network 23, in a further embodiment, one or more other actions of the artificial intelligence module 37 can require confirmation by a user from the relevant healthcare facility prior to being implemented, thus creating an effect of artificial intelligence augmented by humans. Further, the entirety of the stakeholder (health care facility staff member) workflow, from pre-intake to post-intake, is taken into account when replacing the non-patient interfacing and patient-facing functions of healthcare staff members, while solving the healthcare facility staff members' pain points. Hence, the entire user experience (UX) is human engineered, being assisted by the machines, but with human perceptions and empathy still being at the forefront of the execution of the system 10.

One or more of the background servers 13 further executes a payment module 205 that a patient can use to securely make a payment via a credit (or debit) card. If a patient payment for a bill is not received within a predefined period of time (such as the time period indicated on the bill 41), the artificial intelligence module can use the large language model 38 to generate a collection notice that is provided by the chatbot 39 as one of the messages or through another medium.

Figure 13:
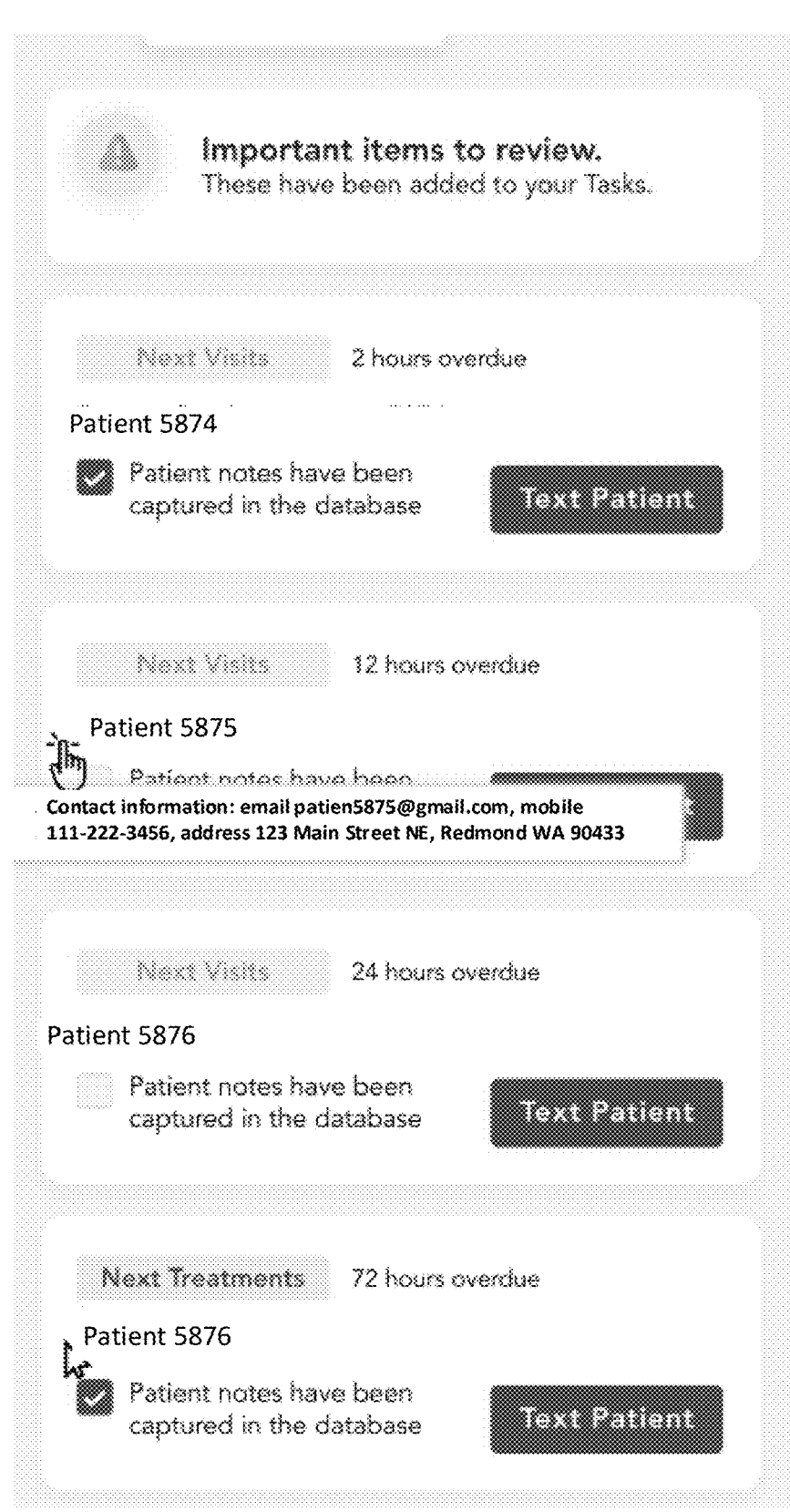
FIG. 13 is a diagram showing, by way of example, a user interface presenting a list of patients that need to be contacted in a form of a checklist.

While the artificial intelligence module 37 and the chatbot 39 in particular can formulate messages 46 automatically, the messages 46 can also be generated based on prompts provided as part of user input 202, such as by users from the healthcare facility at which the appointments happen, interacting with the chatbot either through the computing device 25 of the clinic (such as through the PRMS 26) or through other channels (such as dedicated mobile application, a web browser, or other mediums) on one or more additional computing devices (not shown). For example, the healthcare facility users can provide prompts (such as textual directions) to the chatbot to generate and send particular kinds of messages 46, such as e-mails with particular content to particular patients or particular kinds of patients (such as patients who have not confirmed their appointments and patients who have not scheduled a particular kind of treatment in a particular time period (such as patients who have not scheduled a teeth cleaning in the last six months). Similarly, the healthcare facility users can direct to the artificial intelligence module requests to retrieve particular kinds of data or a particular patient), with the artificial intelligence interpreting the questions natural language processing, finding the required data in the relational database for the healthcare facility associated with the requesting user, and generating a response using the large language model 38. The artificial intelligence module 37 can also recommend initiating contact with certain patients with particular patients (such as patients who recently had an appointment and need a follow-up or who are overdue for treatment) at particular time points, such as at the end of every day, as seen with reference to FIG. 13. FIG. 13 is a diagram showing, by way of example, a user interface 180 presenting a list of patients that need to be contacted in a form of a checklist.

Further, the actions of the artificial intelligence module 37 (and possibly other modules implemented by the backend servers 13) can be triggered by the actions of the patients. For example, a patient can via a mobile app executed on the computing device 17 change his or her insurance provider information, which are provided to the artificial intelligence module 37. Upon receiving that information, the artificial intelligence module 37 automatically contacts the insurance server 19 to receive most up-to-date information regarding the patient's insurance benefits and automatically updates all related information that is stored in the relational database 32. The artificial intelligence module will further provide the updated insurance information to the PRMS 26, which will in turn update both the insurance information and any related copays in the appropriate sections of the PRMS 28 data. Similarly, if the staff members of the healthcare facility access the web portal 31 in ways other than through the PRMS 26 (such as through a mobile app implemented on their individual computing devices), the data presented to these staff members via the web portal 31 will also reflect the updated information. Likewise, the web portal 31 presented to the patient will also reflect these updates, and thus the patient will be aware of any changes (such as new copays) that arise from the change ahead of the appointment. Upon making the updates, the artificial intelligence module 37 will also create a record, such as account note that describes all of the updates made, and that is available to authorized users. Thus, because the updates were performed and communicated without requiring involvement of the staff of the health care facility, the updates were done almost instantaneously and with reduced potential for error compared to if a human was involved, achieving a real-time synchronization of data in all relevant data storages and presentation mediums. Other actions by the artificial intelligence module 37 can similarly be activated by the patient and staff members of the healthcare facility.

The artificial intelligence module 37 can further perform analysis of available financial data of the healthcare facility to help avoid fraud and embezzlement. In particular, the artificial intelligence 37 can generate messages 46, including alerts, provided to the responsible person of at the healthcare facility (such as through the PRMS 26, dedicated mobile application, web browser, text messages, e-mails, or other communication techniques) regarding the financial data. Such messages 46 can include reports of collection performance, including payment tracking, cash accountability, control payment plans, claim status monitoring, and other financial analytics processing, thus providing an integrated back office. The alerts can be based on used the artificial intelligence module 37 having been trained on training data 209 where certain financial patterns are labeled as being associated with possible fraud or embezzlement or other negative outcomes.

While certain kinds of appointment data 36 are described above, other kinds of appointment data are possible. Such additional appointment data 36 can include tracking of the time the patient arrives to the healthcare facility, and is done with the procedure, though still other kind of appointment data is also possible.

The cloud-computing environment 11 vastly reduces the number of non-patient interfacing tasks that staff members of the healthcare facility have to perform as well while making the receipt of healthcare at the healthcare facility far more transparent. In addition to receiving patient data from the relational database of the healthcare facility when needed, a user of PRMS 26 can further retrieve such patient information when desired, thus providing seamless access to a wealth of information that could be useful when treating a particular patient. However, based on the appointment data 36 and other kinds of patient data 33, the cloud-computing environment 11 further analyzes the performance of individual staff members at the healthcare facilities who are responsible for those appointments and care of those patients. The relational database 32 for each healthcare facility also stores data 206 for one or more (or all) of the staff members working at that healthcare facility. The staff member data 206 can include name of the staff member, at least one unique identifier of the staff member (such as an employee ID number, an identifier of the staff member within the PRMS 26, or an identifier of that staff member within the cloud-computing 11), the staff member's role (such as a provider (dentist, doctor, nurse, dental hygienist or another kind of provider), assistant (such as dental assistant or medical assistant), or administrative assistant, though other kinds of roles are also possible), traits of the staff members (such as years of experience they have and the time that they have worked at that particular healthcare facility), and any set performance goals by staff member. The staff member data 206 can further include weekly workdays and work hours of the particular staff member, which can be used in scheduling of the appointments. Other kinds of staff member data 206, including staff member preferences, are also possible. Staff member data 206 can be set by the staff member via a settings page of the web portal 31 (accessed through a mobile application, through the PRMS 26, or through another medium) or by another authorized user. Associated with both the healthcare facility are also a plurality of key performance indicators (KPIs) 207 that are determined by the artificial intelligence module 37 based on the patient data 33 (including appointment data 36) in the relational database 32 of that healthcare facility. The artificial intelligence module 37 further determines the KPIs for the individual staff members whose data 206 is listed in the database 32 based on the data 33 for patients with whom those staff members interact. While the exact KPIs 207 may vary based on the nature of practice of a particular healthcare facility and what are considered measures of success in that practice as well as a staff member's role in that practice, in one embodiment, the KPIs 207 for a dentist can include production (dollar amount earned by that provider for the healthcare facility during a particular period of time), collections (how much of the earned amount was collected, which can depend on how correctly the billing for the appointments was done); recall (the rate at which patients come for cleaning to the provider); patient case acceptance (the rate at which a patient decides to accept a treatment recommended by the provider); cancellation rate of appointments with the provider, capacity (the dollar amount of the cost of the procedures that the provider is able to perform during a particular time frame; as more complicated procedures bring in a higher dollar amount, this KPI 207 is indicative of how quickly the provider is able to perform procedures of high complexity); a number of new patients that the provider has gained; monthly staff goal (whether the provider has gained a particular goal that can be stored as part of the staff data 206 for that provider); seat time (any lag between the time the appointment is scheduled and the time patient is actually seated in the dental chair for the procedure), and monthly (or another time length) satisfaction of the provider with the provider's job Other KPIs 207 are also possible. For example, KPIs 207 that are for a health clinic as a whole can include employee saturation (degree to which employees are utilized to their maximum capacity and ability), the degree to which complicated procedures (high cost procedures) are combined with simple procedures (low cost procedures) on the same day, and the timeliness on which staff members of different roles overlap on the same procedures (for example, one procedure can require half hour of assistant time in the beginning and half hour of provider time at the end). Staff job satisfaction is the only KPI 207 that must be solicited by the backend servers 13 directly from individual staff members (either through the PRMS 26 or through individual computing devices of those staff members). All other KPIs 207 can be derived based on the data stored in the relational database 32 for the facility. The KPIs can be presented in graphical form, as can be seen with reference to FIG. 11, either through the PRMS 26 or through individual computing devices of users associated with the healthcare facility (such as through a dedicated mobile application through which the web portal 31 is accessed, a web browser through which the web portal 31 is accessed, text messages, e-mails, or other kinds of messages). FIG. 11 is a diagram showing, by way of example, a screenshot of a user interface 140 of the web portal 31 through which the KPIs are presented in graphical form.

While some dental staff members may not have all of the same KPIs 207, some KPIs do remain consistent among staff members of different roles. For example, capacity 207 is a KPI 207 that remains consistent among multiple dental staff roles and is particularly useful in arranging staff schedule. When multiple staff members have the same KPIs 207, an aggregate of those shared KPIs 207 for the staff members is the value of that shared KPI 207 for the clinic as a whole.

The artificial intelligence module 37 analyzes the KPIs 207 and creates actionable insights 208 for individual staff members for improving those KPIs 207. As described above, the artificial intelligence module is trained using training data 209, and for purposes of training the artificial intelligence module to improve the KPIs 207, the training data 209 can include particular actions that were taken at a similar healthcare clinic in the past by staff personnel with particular roles and traits and the effect those actions had on particular KPIs. Once trained using this training data 209, the artificial intelligence module prepares actionable insights 208 (such as recommendations to perform particular actions at a particular time,) based on actions recorded in the training data 209 that helped staff members in similar circumstances improve their KPIs 207 from similar levels. Such insights 208 can range from areas like how to schedule a provider's appoint to how quickly a room in a healthcare facility should be cleaned after a patient uses the room. Such actionable insights 208 can be presented as messages 46 composed and provided by the chatbot 39 to the staff members either through the PRMS 26 or through individual computing devices of the staff members (such as through a dedicated mobile application through which the web portal 31 is accessed, a web browser through which the web portal 31 is accessed, text messages, e-mails, or other kinds of messages).

The actionable insights 208 can also be directed to the healthcare facility as a whole, with the training data 209 for the artificial intelligence module 39 including data describing what actions resulted in increased KPIs for the healthcare facility with certain traits (such as having a certain number of staff members with certain roles and traits). After being trained with this training data 209, the artificial intelligence module 37 generates the actionable insights for the healthcare facility (including creating messages 46 by the chatbot 39 using the large language model 38 describing these actionable insights) and provides the actionable insights 208 to the staff member in charge of the healthcare facility (such as a dentist in a dental office). If the healthcare facility is a small one (having only one provider), the insights 208 generated for the facility as a whole are provided to person in charge as part of the person's individual insights. Such insights can include when to hire additional staff members (such as hygienists, front office and assistants, which days have the heaviest schedule saturation, when to launch marketing, which staff is the slowest and not place them when the schedule is the heaviest, which staff combination works the best with which type of schedule combination and saturation, which doctor or hygienist patient prefer and make sure the right provider is working that day, though other insights 208 are also possible. For example, the insights 208 related to the facility as a whole includes can relate to inventory tracking. For example, if a particular product used during a particular procedure has not been reordered within a particular time frame and more appointments for the procedure are coming up, an insight can be to reorder the product. In one embodiment, the staff members perform the actually product ordering themselves. In a further embodiment, upon receiving the approval of the user, the artificial intelligence module (or another module implemented by the backend servers 13) can perform the ordering, thus implementing automatic inventory restocking.

In addition to having the ability to generate actionable insights 208 due to being trained on training data, the artificial intelligence module 37 can further generate the insights 208 for both the individuals and the facility as a whole based on forecasts business needs of the healthcare facility, such as the number of staff that need to be at the facility at a particular day. The forecasts can be based on the individual KPIs 208 of the staff, especially capacity. For example, if a large number of patients wants to schedule complicated appointments for a particular day, a large number of staff with a high capacity KPI needs to work in the healthcare facility that day.

Further, a third source of information that can be used by the artificial intelligence module 37 in generating actionable insights is institutional knowledge 210 stored in the relational database 32 of the healthcare facility for which (and for whose staff members) the insights 208 are generated. The institutional knowledge 210 is collection of best practices for the particular kinds of healthcare facility, such calling ahead if a preauthorization is not received for a crown procedure, texting a patient who needs to leave at a certain time if an opportunity to move the appointment up arises, and texting patients (which can be identified by the artificial intelligence module 37 based on having appointments scheduled in the near future) who could fill in a last minute cancellation. The institutional knowledge 210 can be loaded into the database 32 by an administrator of the cloud-computing environment 11, a staff member in the healthcare facility associated with the database 32, or both.

Figure 14:
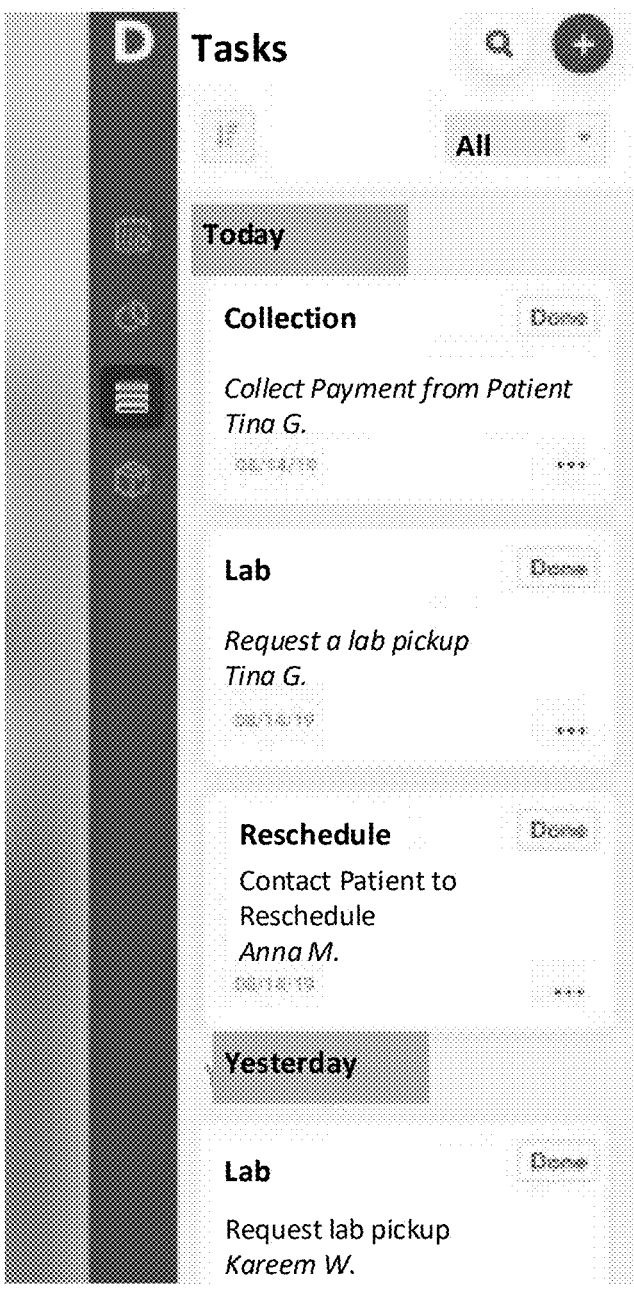
FIG. 14 is a diagram showing, by way of example, a user interface of the web portal presenting tasks for different staff members to optimize their healthcare facility schedule.
Figure 15:
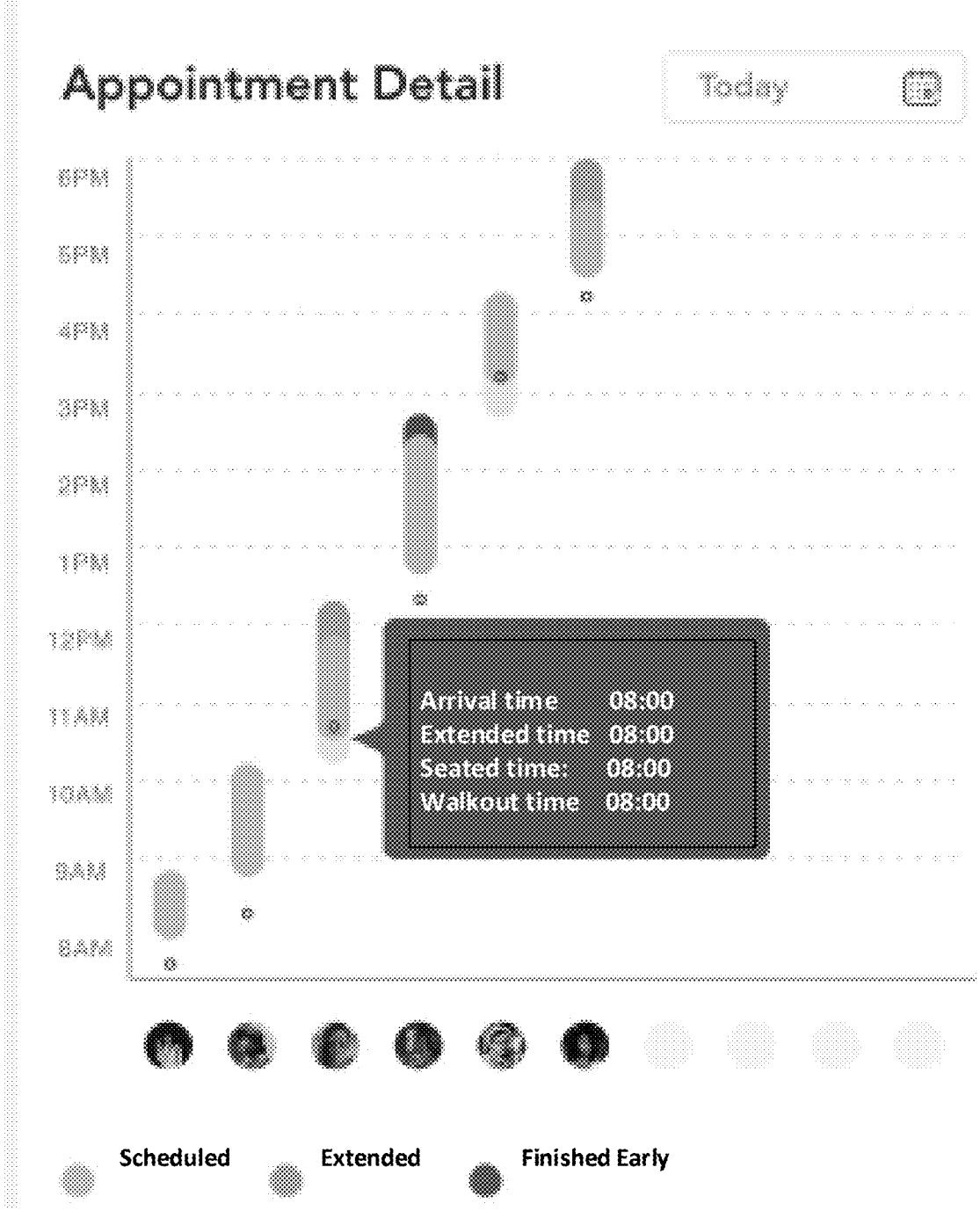
FIG. 15 is a diagram showing, by way of example, a user interface of the web portal showing a graphical representation of a schedule for appointments for a day at a healthcare facility.

While actionable insights can be useful in many areas, one particular area where actionable insight 208 can that affect many KPIs 207 is schedule optimization for the healthcare facility. Such schedule optimization can include providing alerts regarding bottlenecks (times when the provider is running late with appointments), openings for today and particular days, how to overlap procedures to minimize wait time and running late, how to fill and avoid openings, optimal appointments to obtain optimal production (saturation), report and advise how to optimize interactions during check in and check out, how to improve case acceptance and recall cleaning scheduling, how to decrease a new patient onboarding time, and increase laboratory coordination to ensure lab results and delivery. Such insights 208 can be presented as a series of tasks for individual staff members, as seen with reference to FIG. 14. FIG. 14 is a diagram showing, by way of example, a user interface 190 of the web portal 31 presenting tasks for different staff members to optimize their healthcare facility schedule. The resulting schedule (both before the scheduled appointment take place and after the appointments take place) can also be presented in graphical form, as seen with reference to FIG. 15. FIG. 15 is a diagram showing, by way of example, a user interface 190 of the web portal 31 showing a graphical representation of a schedule for appointments for a day at a healthcare facility.

Figure 9:
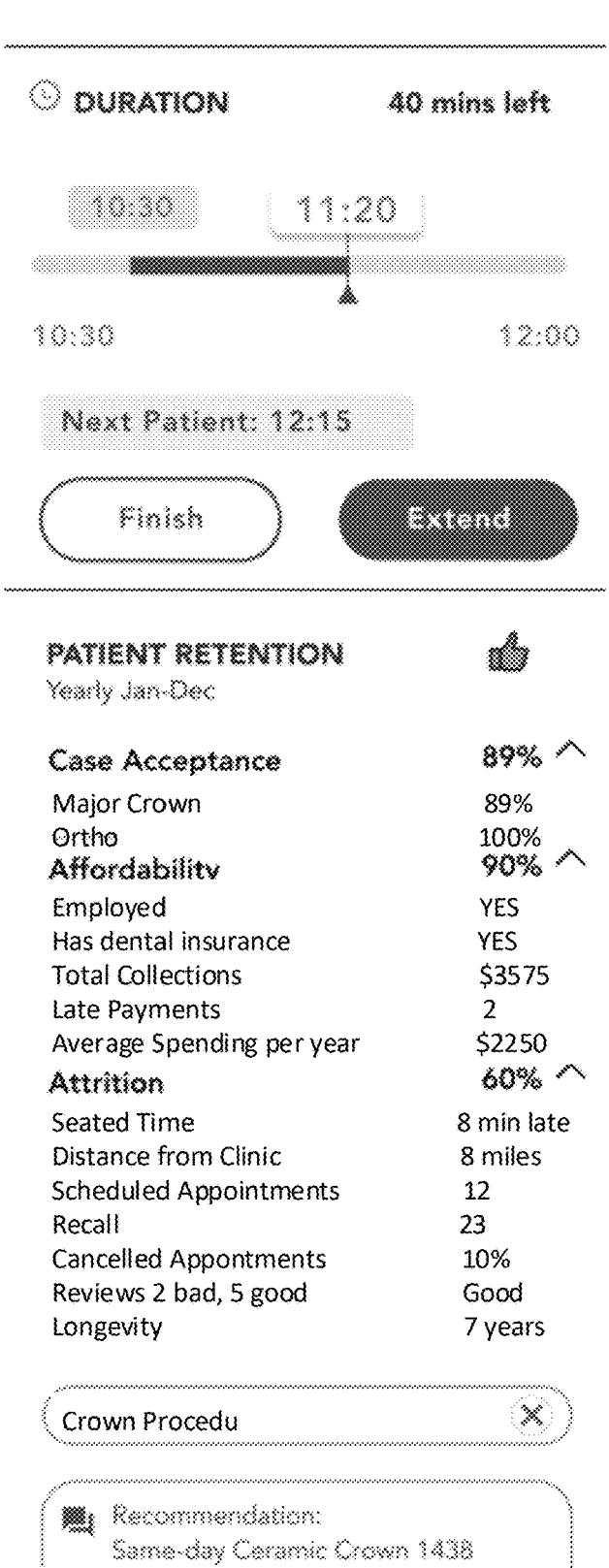
FIG. 9 is a diagram showing, by way of example, a user interface of a web portal showing patient traits.
Figure 10:
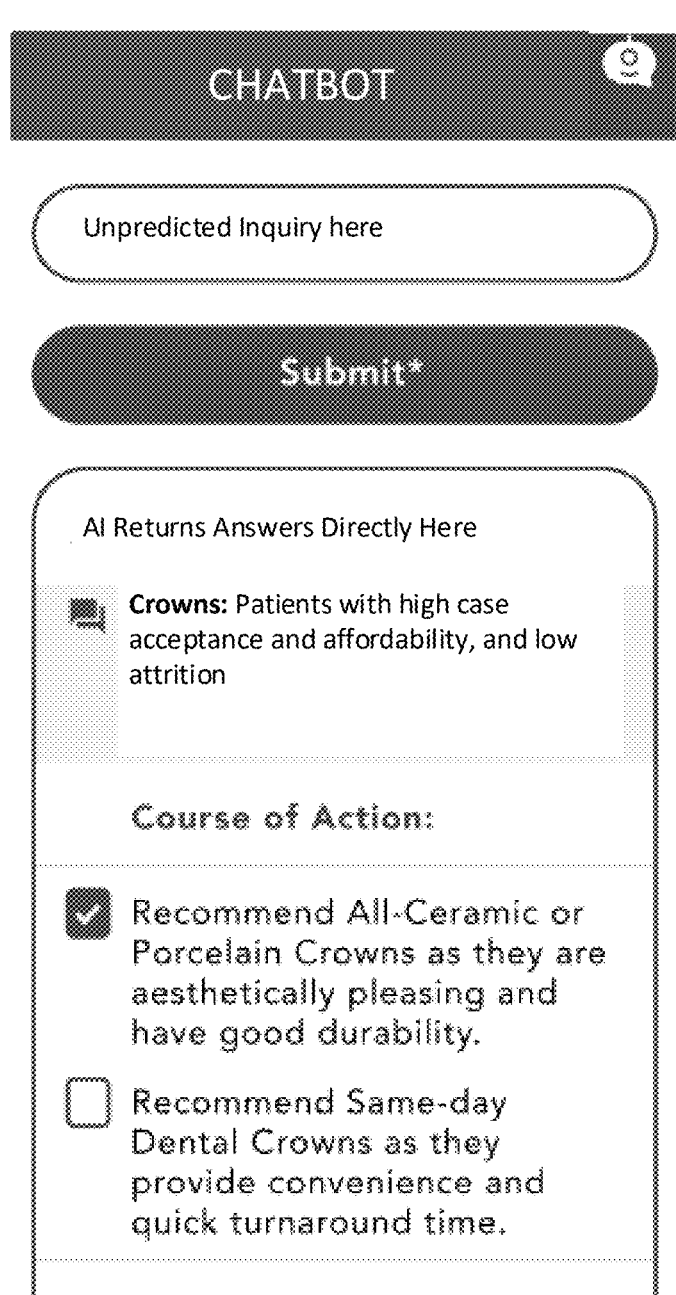
FIG. 10 is a diagram, showing by way of example, a user interface for interacting with the chatbot that can be presented through the web portal and through which an insight 208 is presented.

While actionable insights 208 can focus on multiple patients at once, actionable insights can also be focuses on a specific patient. In particular, based on the patient's data 33, the artificial intelligence module 37 can derive particular traits of the patient that are presented as part of the insight 208 regarding the patient, as seen with reference to FIG. 9. FIG. 9 is a diagram showing, by way of example, a user interface 110 of a web portal 31 showing patient traits. The traits include data regarding an ongoing appointment but also include traits derived based on historical patient data 33, such as case acceptance (rate at which the patient accepts recommended treatment for different categories of treatment), affordability (the financial ability of the patient to pay for different treatment, such as the patient's employment status, payment history, and having dental insurance), and attrition (describing previous appointments of the patient at the facility, patient's rating of those appointments, how far the patient lives from the facility, and how long the patient has been visiting the facility). The patient data 33 regarding which such traits are derived can include past crown, filling or ortho procedures, frequently of cleaning, cleaning compliance, how long the patient has been visiting the healthcare facility, whether the patient's insurance is via the patient's employer or individual or Medicare, and outstanding balance, though other patient data on which the traits are derived are also possible. Based on these traits, when there are multiple options for treatments, the artificial intelligence module 37 provides an insight 208 of which option the patient is most to accept, as seen with reference to FIG. 10. FIG. 10 is a diagram, showing by way of example, a user interface 130 for interacting with the chatbot 39 that can be presented through the web portal 31 and through which an insight 208 is presented. This insight 208 is determined using machine learning, after the artificial intelligence module 37 has been trained on training data 209 that included patients with similar traits and which treatment option they accepted.

Figure 12A:
FIGS. 12A-12C are diagrams showing, by way of example, user interfaces in which insights with emotionally supportive statements are presented.
Figure 12B:
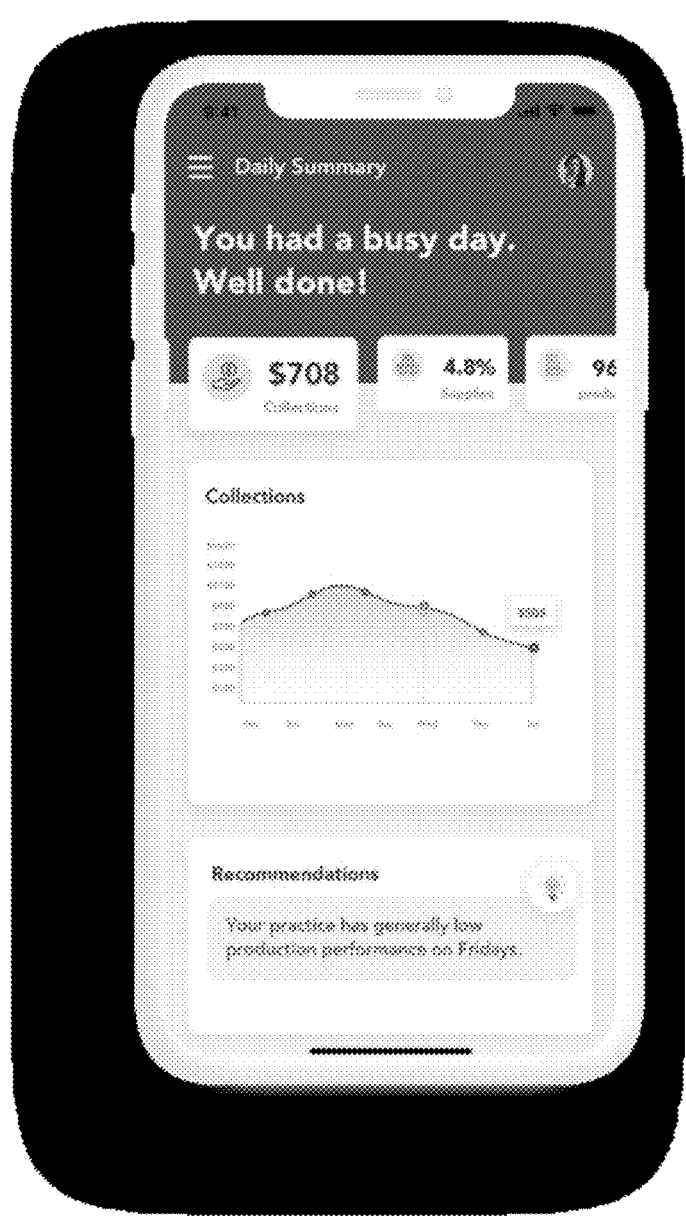
Figure 12C:
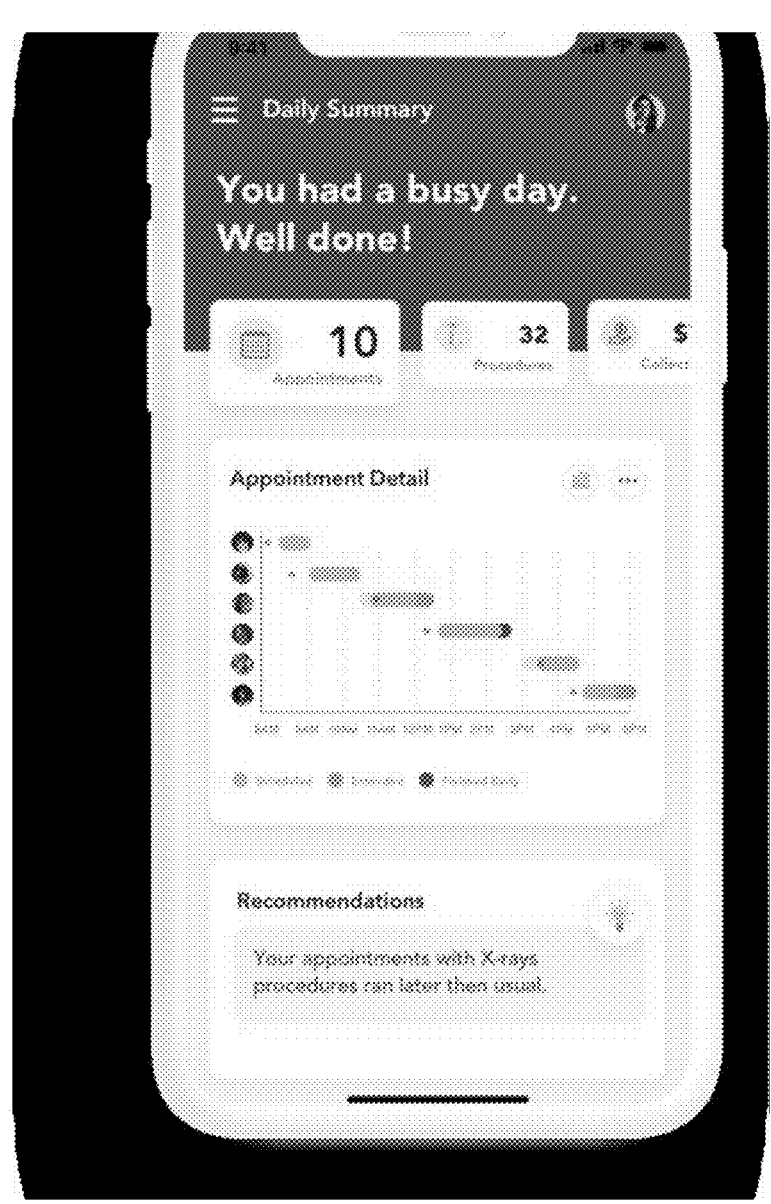

The generated actionable insights 208 are generated to promote modeling (providing a role model), mentoring, coaching, motivating, and multiply mentoring (encouraging the individual to teach others) while being emotionally supportive of the individual. As can be seen with reference to FIGS. 12A-12C, the insights 208 can include emotionally supportive statements and include acts that increase the individual's emotional comfort (such as setting up supportive photos in the individual's workspace), thus allowing to increase staff work satisfaction and decrease staff turnover. FIGS. 12A-12C are diagrams showing, by way of example, user interfaces 150-170 in which insights 208 with emotionally supportive statements are presented. Similarly, the artificial intelligence module 37 can use the staff members traits to recommend the best educational resources to accelerate their onboarding and improvement, such a insights 208 to watch particular educational videos.

The physical servers and databases implementing the cloud computing environment 11 as well as computing devices 17 and 25 can include components found in programmable computing devices, such as one or more CPUs, GPUs, memory, input/output ports, network interfaces, and non-volatile storage, although other components are possible. The modules 16, 18, 37, 201, 204, 205, and the Web API 22 implemented by the respective servers 12, 13 can be implemented as a computer program or procedure written as source code in a conventional programming language and that is presented for execution by the central processing unit as object or byte code. Alternatively, at least some of the modules could also be implemented in hardware, either as integrated circuitry or burned into read-only memory components, and each of the servers 12, 13 can act as a specialized computer. For instance, when the modules are implemented as hardware, that particular hardware is specialized to perform the communications and analysis that other computers without the hardware cannot be used for that purpose. The various implementations of the source code and object and byte codes can be held on a computer-readable storage medium, such as a floppy disk, hard drive, digital video disk (DVD), random access memory (RAM), read-only memory (ROM) and similar storage mediums. Other types of modules and module functions are possible, as well as other physical hardware components. While the computing devices 17 and 25 are shown with reference to FIG. 1 to be a mobile phone and a server respectively, other kinds of computing devices 17, 25 such as desktop computers, smartphones, and tablets, are possible. Similarly, the reverse proxy server 24 can be implemented as a laptop computer, a desktop computer, or another type of computing device.

In one embodiment, a single frontend server 12 can contribute to the execution of all of the Web API 22, the patient module 16, and the insurance module 18. The Alternatively, a single frontend server contributes to execution of only one or two of the Web API 22, the patient module 16, and the insurance module 18. Likewise, a single backend server 13 can contribute to the execution of all three modules 37, 201, 204. Alternatively, a single background server 13 can contribute the execution of only one or two of the modules 37, 201, 204.

In a further embodiment, some of the data that is shown as stored in the relational database 32 and 213 (such as insurance data 44 and data relating to machine learning by the artificial intelligence module 37) can be consumed as json and csv files stored within the cloud-computing environment 11. Access to such files is restricted to authorized services executed by the servers 12, 13 as well as only IP addresses from an allowed list.

Figure 2:
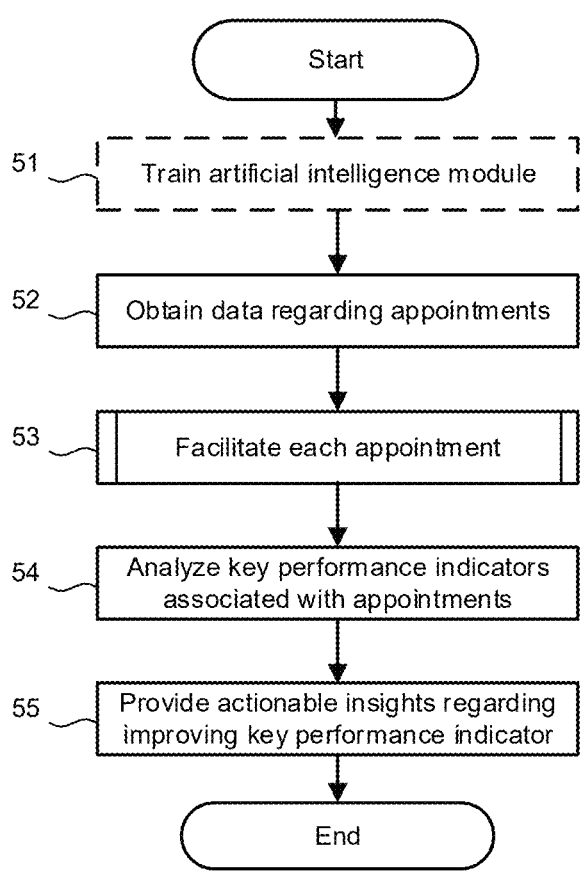
FIG. 2 is a diagram showing a method 50 for artificial-intelligence-driven healthcare practice management in accordance with one embodiment.

By reducing the amounts of administrative tasks that healthcare personnel have to do as well as providing data-driven suggestions for improving their performance, the quality of patient care and the willingness of patients to receive such care can be improved. FIG. 2 is a diagram showing a method 50 for artificial-intelligence-driven healthcare practice management in accordance with one embodiment. The method 50 can be implemented using the system 10 described above with reference to FIG. 1. Optionally, if not already done before during previous iterations of the method 50, the artificial intelligence module is trained using training data, as described above (step 51). Data 33, 36 regarding a plurality of appointments at a healthcare facilities and patients undergoing treatment during those appointments is obtained by one or more of the backend servers 13, as described above (step 52). Each of the appointments is facilitated by the cloud-computing environment 11, as further described in detail beginning with reference to FIG. 3 (step 53). Key performance indicators 207 associated with the appointments are obtained by the artificial intelligence module 37 using the data 33, 36 associated with the patients and the appointment and direct contribution of relevant healthcare staff, as described above (step 54). Actionable insights 208 are generated through analyzing KPIs through machine learning, using KPIs for making forecasts regarding the healthcare facility in question, and institutional knowledge 210, as described above, and are provided to the staff at the healthcare facility (step 55) ending the routine.

Figure 3:
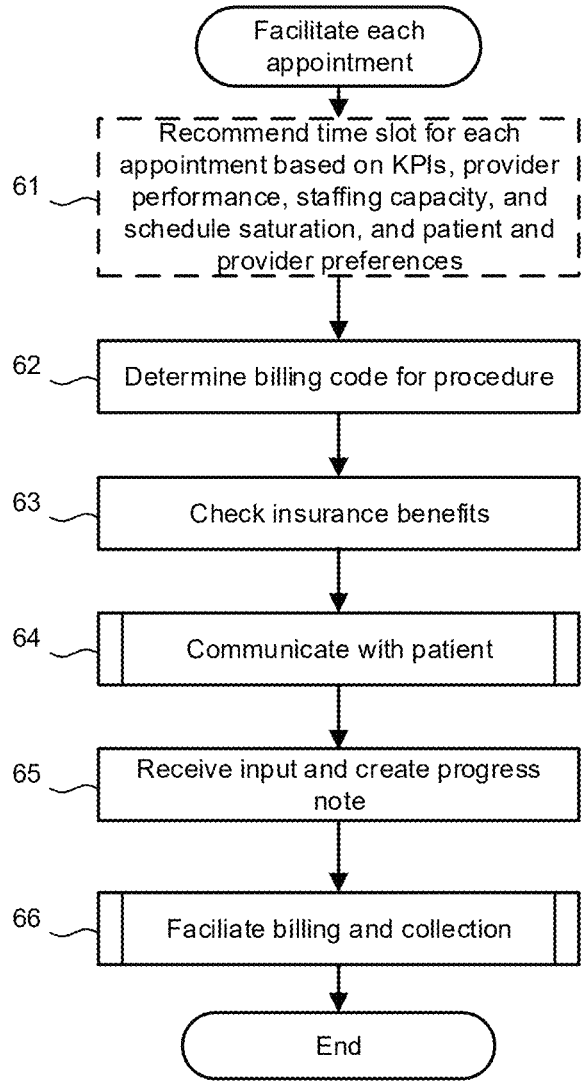
FIG. 3 is a flow diagram showing a routine for facilitating appointments for use in the method of FIG. 2 in accordance with one embodiment.

Facilitation of appointments by the cloud-computing environment 11 increases transparency of receiving healthcare treatments for the patient and decreases the administrative burden on the staff of the healthcare facilities. FIG. 3 is a flow diagram showing a routine 60 for facilitating appointments for use in the method 50 of FIG. 2 in accordance with one embodiment. Optionally, if not set by the healthcare facility, one or more of the backend servers 13 recommend a time slot for each appointment based on one or more of KPIs for the healthcare facility, provider performance, staffing capacity, and schedule saturation, and patient and provider preferences (step 61). Billing code 41 for the procedure is determined by the artificial intelligence module 37, as described above (step 62). Insurance benefits for the patient are checked by one or more of the backend servers 13, as described above (step 63). Communication with the patient is performed using the chatbot 39, as further described below with reference to FIG. 4 (step 64). Input from a user associated with the healthcare facility performing the appointment is received and a progress note 203 for the appointment is generated by the artificial intelligence module 37 using the large language model 38 (step 65). Billing and collection for the procedure is facilitated, as described below with reference to FIG. 5 (step 66), ending the routine 60.

Figure 4:
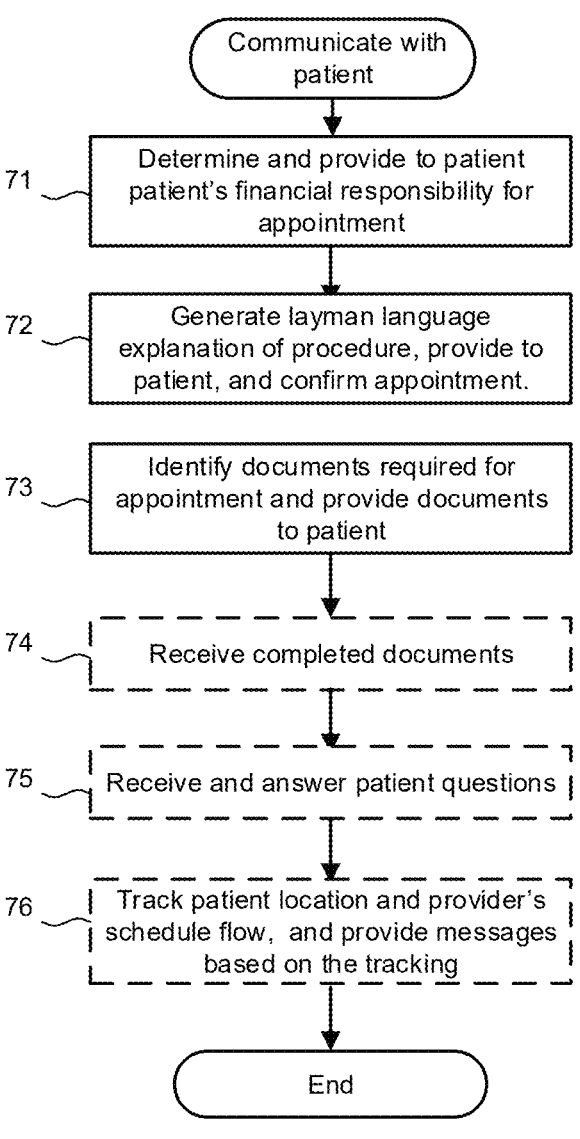
FIG. 4 is a diagram showing a routine for communicating with the patient for use in the routine of FIG. 3 in accordance with one embodiment.

Near-instantaneous communication with the patient, including answering the patient's questions, increases the likelihood that the patient will seek and accept recommended treatment. FIG. 4 is a diagram showing a routine 70 for communicating with the patient for use in the routine 60 of FIG. 3 in accordance with one embodiment. Patient's financial responsibility for the appointment is determined using the billing code 41 and the insurance benefits along with any optional payment plan for the patient's financial responsibility are determined by the artificial intelligence module as described above (step 71). The layman language explanation of the procedure is generated as described above by the artificial intelligence module 37, with the layman language explanation being provided to the patient via the computing device 17 by the chatbot 39, and the time for the appointment is confirmed (step 72). The provision of the patient financial responsibility (along with any payment plan) can occur at the same time as the provision of the layman language explanation of the procedure. Documents associated with the procedure to be performed are identified by the artificial intelligence module 37 and provided to the patient via the computing device 17 (step 73), with completed documents being optionally also received by the artificial intelligence module and stored in the database 32 (step 74). In a further embodiment, print copies of the completed documents are brought by the patient to the healthcare facility and provided to the cloud-computing environment as part of PRMS data 28. Optionally, if the patient has any questions, the chatbot 39 receives the questions and answers the questions using natural language processing and the data in the database 32 (step 75). Also optionally, if the patient provides consent, the location tracking module 201 tracks the patient's locations and the chatbot 39 provides messages using the tracked location and the provider's schedule flow, as described above (step 76), ending the routine 70.

Figure 5:
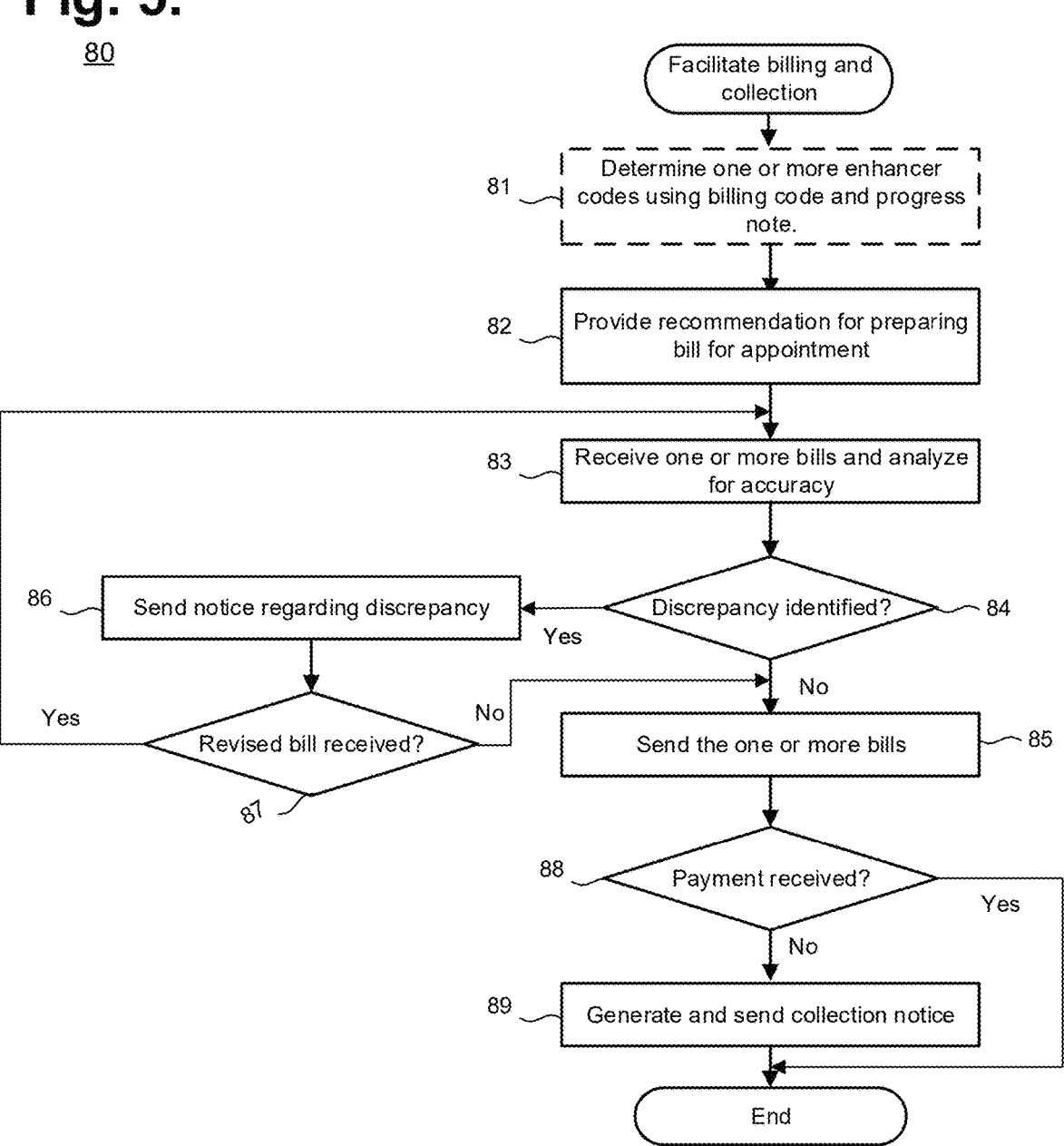
FIG. 5 is a flow diagram showing a routine for facilitating billing and collection for use in the routine of FIG. 3 in accordance with one embodiment.

Facilitation of billing through the use of artificial intelligence reduces the likelihood of mistakes in the billing and increases the likelihood of the healthcare facility being paid for their services within a reasonable time. FIG. 5 is a flow diagram showing a routine 80 for facilitating billing and collection for use in the routine 60 of FIG. 3 in accordance with one embodiment. Optionally, if the procedure performed at an appointment is a medical procedure and an enhancer code 41 is appropriate, an enhancer code is generated by the artificial intelligence module for the procedure based on the billing code 41 and the progress note 203 for the procedure (step 81). A recommendation one or more bills for the procedure is made by the artificial intelligence module, as described above (step 82). One or more bills are received by the artificial intelligence module and are analyzed for any discrepancy between the bills and the billing code, the enhancer code, the patient's insurance coverage, or other information in the relational database 32 (step 83). If no discrepancies are revealed (step 85), the artificial intelligence module 37 sends the one or more to the appropriate parties. If any discrepancies are revealed (step 84), a notice regarding the discrepancy is sent by the artificial intelligence module 37 to the party that provided the bill (step 84), such as a user of the PRMS 26 of the healthcare facility. If a revised bill is received (step 87), the routine returns to step 83. If no revised bill is received within a predefined period of time or the user who provided the bill confirms that the bill is to be sent (step 87), the artificial intelligence module sends the bill (step 85). If payment is received within a predefined period of time (step 88), the routine 80 ends. If the payment is not received within the predefined period of time (step 88), the artificial intelligence module 37 generates and sends the collection notice to the non-paying party (step 89), ending the routine 80.

While in the descriptions above, the cloud-computing environment is described as communicating with the patient, when the patient is incapacitated or a minor, the cloud-computing environment 11 could be communicating with a representative or guardian of the patient in the same way.

While the invention has been particularly shown and described as referenced to the embodiments thereof, those skilled in the art will understand that the foregoing and other changes in form and detail may be made therein without departing from the spirit and scope.

What is claimed is:

1. A system for artificial-intelligence-driven healthcare practice management, comprising:

a cloud-computing environment comprising a plurality of servers, the servers comprising one or more frontend servers and one or more backend servers, each of the backend servers interfaced to at least one of the frontend servers, the cloud-computing environment further comprising:

at least one of the frontend servers configured to receive data regarding an upcoming appointment for a healthcare procedure for a patient and information regarding insurance for the patient, the appointment data comprising a description of the procedure, one or more of the frontend servers further configured to execute a web application programming interface (API) that is configured to identify a local network associated with the healthcare facility that comprises a computing device executing a practice management software and interfaced to one or more databases storing local network data, to periodically send a request for some of the local network data from a reverse proxy server associated with the local network of the healthcare facility, and to provide the appointment data to one or more of the backend servers following receipt of the local network data that comprises the appointment data and a request for the appointment data by the one or more of the backend servers, wherein each of the local network data requests comprises an external reference to a location of the requested local network data within the local network, and wherein the appointment is one of a plurality of appointments at the healthcare facility associated with a plurality of healthcare staff members during a time period;

one or more of the backend servers implementing an artificial intelligence module and configured to:

use the artificial intelligence module to determine a billing code associated with the procedure using the description of the procedure; and determine a payment associated with the procedure that the patient is responsible for using the billing code and the insurance information;

send a message regarding the payment to a computing device associated with the patient via one of the frontend servers;

determine a plurality of key production indicators (KPIs) associated for one or more of the healthcare staff members using at least a portion of the data regarding the appointments associated with those healthcare staff members;

use the artificial intelligence module to generate a recommendation for improving one or more of the KPIs; and provide the determined KPIs and the recommendation to the computing device associated with the healthcare facility via one of the frontend servers; and the reverse proxy server configured to receive the local network data requests, to convert each of the external references to a reference to an internal structure of the local network, to retrieve the requested local network data using the internal structure references, and to provide the requested local network data to the web API together with the request for that local network data.

2. A system according to claim 1, the artificial intelligence module further comprising a chatbot configured to generate the message regarding the payment and to provide the message to the computing device associated with the patient via the at least one frontend server.

3. A system according to claim 2, the chatbot further configured to identify one or more documents that need to be filled out by the patient prior to the procedure, to provide the identified documents to the computing device associated with the patient via the at least one frontend server, and to receive the filled out documents from the computing device via the at least one frontend server.

4. A system according to claim 2, the chatbot further configured to receive a question regarding the procedure from the computing device associated with the patient via the at least one frontend server, to generate an answer to the question, and to provide the answer to the computing device using the at least one frontend server.

5. A system according to claim 4, wherein the question is regarding one or more of the procedure, an appointment associated with the procedure, and a balance the patient has with a healthcare facility associated with the procedure, the patient's claim history with the healthcare facility, the patient's demographic data, the patient's personal preferences, and a seat time for the procedure.

6. A system according to claim 2, the artificial intelligence module further configured to:

use natural language processing to generate a progress note regarding the procedure based on user input.

7. A system according to claim 6, wherein the input is a voice input and the artificial intelligence module further performs speech recognition on the voice input to generate the progress note.

8. A system according to claim 6, the artificial intelligence module further configured to:

generate an enhancer billing code for the procedure based on the billing code and the report;

provide a recommendation for preparing at least one bill for the procedure based on the billing code, the enhancer code, and the progress note; and send the bill to a computing device associated with a company providing the insurance for the patient via at least one of the frontend servers.

9. A system according to claim 6, one or more of the backend servers further configured to perform one or more of:

generate a further bill for the procedure for the procedure for the patient and provide the bill to the computing device associated with the patient via one of the frontend servers;

perform one of:

process a payment for the further bill from the patient via one of the frontend servers;

generate a collection notice upon not receiving the payment for the bill during a predefined time period and provide the notice to the computing device 10 associated with the patient.

10. A system according to claim 6, the artificial intelligence module further configured to:

receive via at least one of the frontend servers a bill prepared for the procedure;

identify a discrepancy between the procedure and the bill using one or more of the progress note, the billing code, and the information regarding the procedure; and provide a notification regarding the discrepancy via at least one of the frontend servers.

11. A system according to claim 1, wherein the data regarding the procedure further comprises an identifier of the patient and a name of the company providing insurance to the patient, further comprising:

at least one of the backend server configured to request via at least one of the frontend servers from a computing device outside of the cloud-computing environment the insurance information using the identifier and the insurance company name.

12. A system according to claim 1, wherein the appointment is one of a plurality of appointments at a healthcare facility associated with a plurality of healthcare staff members during a time period, at least one of the backend servers further configured to:

determine a plurality of key production indicators (KPIs) associated with the healthcare facility based on at least a portion of the appointments;

use the artificial intelligence module to generate a recommendation for improving one or more of the KPIs; and provide the determined KPIs and the recommendation to at least one computing device associated with the healthcare facility via one of the frontend servers.

13. A system according to claim 12, wherein the KPIs comprise one or more of production, collections, recall, patient case acceptance, cancellation rate, capacity, and number of new patients, monthly staff goal, seat time, and monthly staff satisfaction.

14. A system according to claim 12, wherein the KPIs are associated with one of the healthcare staff members and the recommendation is directed to that healthcare staff member.

15. A system according to claim 12, wherein the recommendation comprises an assignment of the appointments to one or more of the healthcare staff members to avoid schedule openings and schedule bottlenecks for that healthcare staff member.

16. A system according to claim 12, wherein the artificial intelligence module is further configured to predict based on the appointments during a day during the time period a number of the healthcare staff members necessary at the healthcare facility during the appointments.

17. A system according to claim 1, further comprising one or more of the backend servers further configured:

track a location of the patient based on signals from the computing device associated with the patient; and provide via one of the frontend servers at least one further message to the computing device associated with the patient based on the tracked location of the patient.

18. A system according to claim 1, wherein the artificial intelligence module utilizes a large language model.

19. A system according to claim 1, wherein the artificial intelligence module is further configured to receive input based on which one or more further messages are generated and sent.

\* \* \* \* \*